United States Patent [19]

Bresser et al.

[11] Patent Number: 5,225,326
[45] Date of Patent: Jul. 6, 1993

[54] ONE STEP IN SITU HYBRIDIZATION ASSAY

[75] Inventors: Joel Bresser, Bellaire, Tex.; Mary J. Evinger-Hodges, Omaha, Nebr.

[73] Assignee: Research Development Foundation, Carson City, Nev.

[21] Appl. No.: 784,690

[22] Filed: Oct. 28, 1991

Related U.S. Application Data

[63] Continuation of Ser. No. 239,106, Aug. 31, 1988, abandoned.

[51] Int. Cl.$^5$ .............................................. C12Q 1/68
[52] U.S. Cl. ........................................... 435/6; 435/5; 435/7.1; 435/810; 436/501; 436/518; 436/800; 436/808; 424/1.1; 424/3; 935/77; 935/78; 536/23.1; 536/23.5
[58] Field of Search ................. 435/5, 6, 7.1, 810; 436/501, 518, 800, 808; 424/1.1, 3; 536/26-28; 935/77, 78

[56] References Cited

U.S. PATENT DOCUMENTS 4,888,278  12/1989  Singer et al. ................. 435/6

FOREIGN PATENT DOCUMENTS 8504720  10/1985  PCT Int'l Appl. .
8604146  7/1986  PCT Int'l Appl. .

OTHER PUBLICATIONS

Tecott, L. et al., in "In Situ Hybridization: Applications to Neurobiology" (Oxford University) pp. 3–24 (1987).
Ruppert, C., et al. EMBO Journ. 5 No. 8:1897–1901 (1986).
Foldes et al., In Acta Microbioligica Hungarica (1984), 31(4):325–334.
Fujimoto et al., J. Neurosurg. (1989) 70:910–915.
Westin et al., Proc. Natl. Acad. Sci. USA (1982) 79:2490–2494.
Griel et al., Lab. Invest. (1989) 60(4):574–582.
Blick et al., Blood (1984) 64:1234–1239.
Wong et al., Science (1986) 233:461–464.
Wolber, in Laboratory Investigation, vol. 56, p. 88A (1987).
Bresser et al., Chemical Abstracts, vol. 107, abstract 171731W (1987), abstract of Gene Anal. Tech. vol. 4, 89–104 (1987).
Forghani et al., J. Clinical Microbiology, vol. 22, pp. 656–658 (1985).
Harper et al., in Methods in Enzymology (Academic Press, N.Y.) vol. 151, pp. 539–549 (1987).
Harper et al., in Methods in Enzymology (Academic Press, N.Y.), vol. 128, pp. 863–867 (1986).
Singer et al., Biotechniques, vol. 4, pp. 231–250 (1986).
Herrman et al., Hepto-Gastroenterol., vol. 34, pp. 148–151 (1987).
Unger et al., American Journal of Surgical Pathology, vol. 101, pp. 1–8 (1986).
Hopman et al., Histochemistry, vol. 85, pp. 1–14 (1986).
Staeheli et al., Cell, vol. 44, pp. 147–158 (1986).
Hames et al., in Nucleic Acid Hybridization (TRL Press, Washington, D.C.) pp. 3–15 and 174–202 (1985).
Shaw et al., Gene, vol. 4, pp. 77–85 (1984).
Price et al., Federation Proceedings, vol. 34, pp. 2227–2232 (1975).
Moench et al., J. Virological Methods, vol. 11, pp. 119–130 (1985).

Primary Examiner—Amelia Burgess Yarbrough
Assistant Examiner—Ardin H. Marschel

[57] ABSTRACT

A quantitative, sensitive, One-Step In Situ hybridization assay is provided which will detect as few as 1–5 copies of target biopolymer per cell and may be accomplished in 5 minutes to 4 hours. There is provided a simultaneous assay for detecting multiple biopolymers within the same cell.

39 Claims, 14 Drawing Sheets

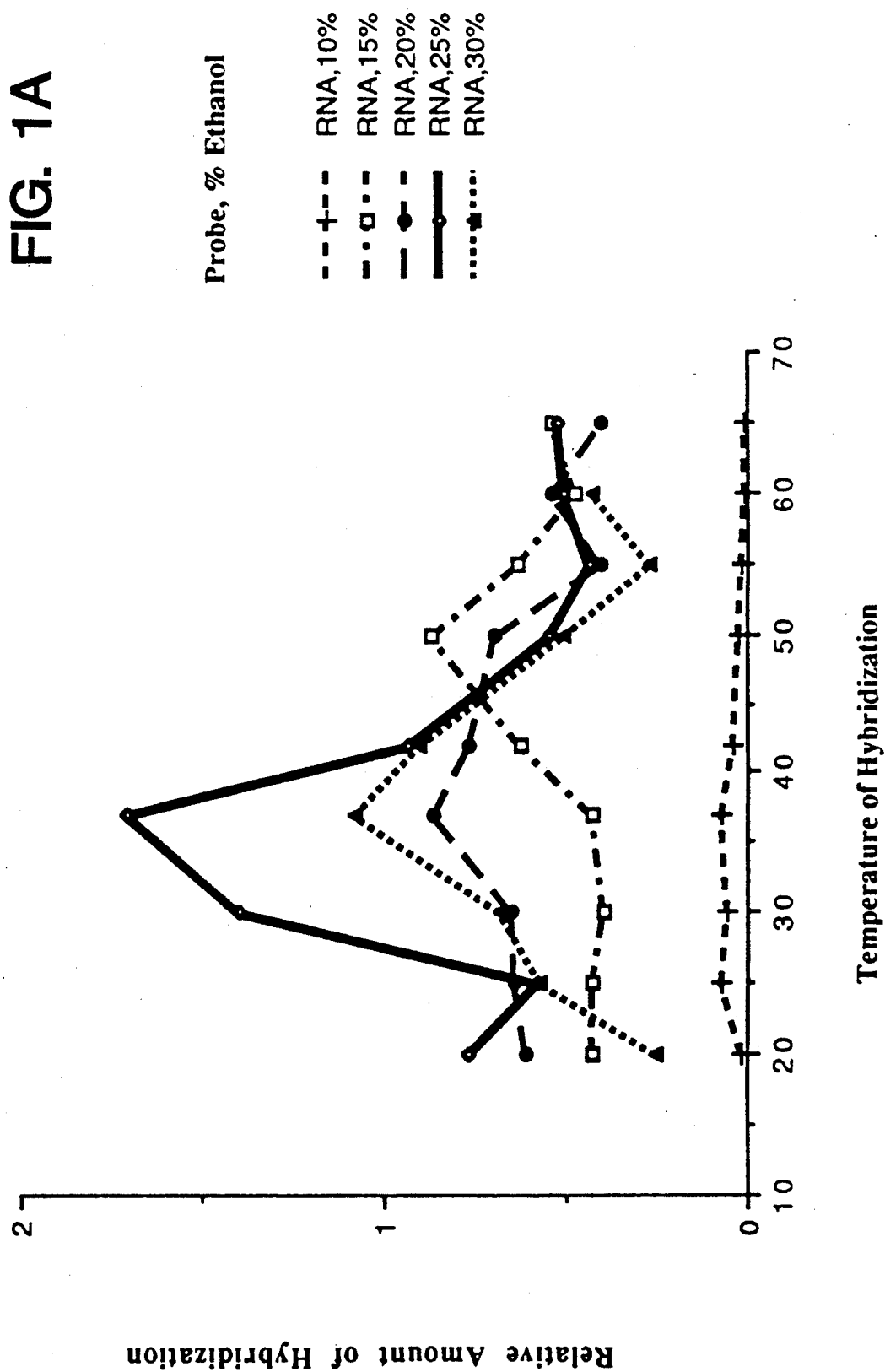

Figure 7A
Figure 7B
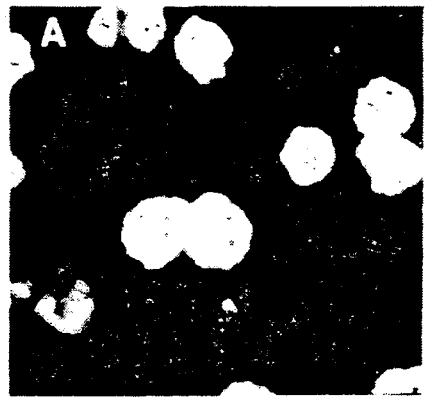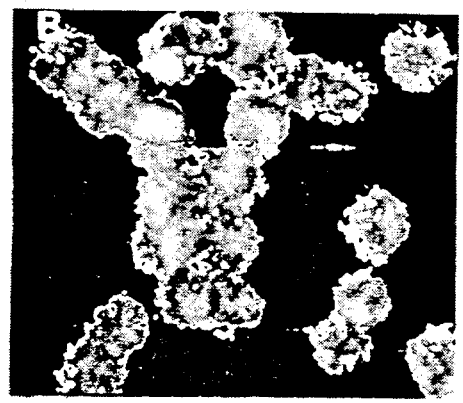
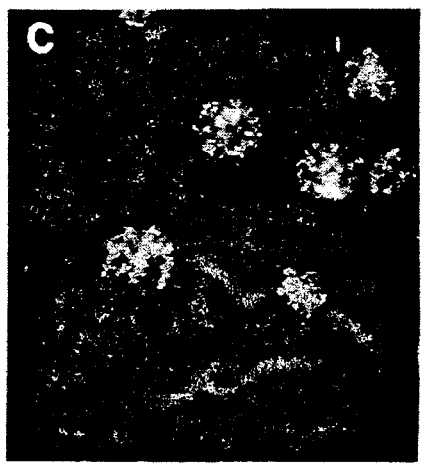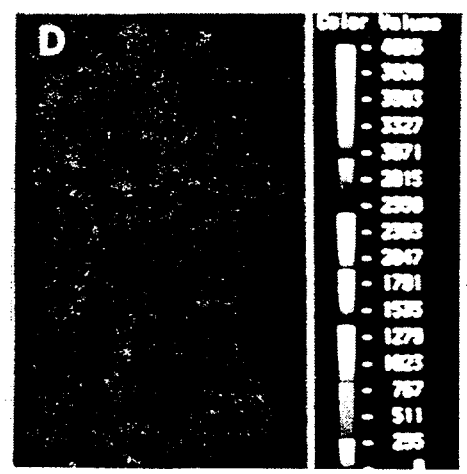
Figure 7C
Figure 7D

Panel 1　　Panel 2　　Panel 3　　Panel 4

Panel 5　　Panel 6　　Panel 7　　Panel 8

ONE STEP IN SITU HYBRIDIZATION ASSAY

This application is a continuation of application Ser. No. 07/239,106 filed Aug. 31, 1988, now abandoned.

BACKGROUND OF THE INVENTION

1. Field of the Invention

The present invention relates to the field of in situ hybridization assays useful for detecting as few as 1-5 copies of target nucleic acid per cell. This assay method significantly increases the sensitivity of detection of nucleic acids over other known methods. In addition, this hybridization method is accomplished with far greater speed than has been reported for other in situ assays. This present invention also provides a method for the rapid and sensitive detection of nucleic acids and proteins in the same cell. A kit is provided for a simple one step fixation/hybridization in situ assay. 2. Description of the Prior Art In situ hybridization provides a technique for the determination and quantitation of biopolymers such as nucleic acids (DNA and RNA) and proteins in tissues at the single cell level. Such hybridization techniques can detect the presence or absence of specific genes in tissues at the single cell level. In situ hybridization procedures may also be utilized to detect the expression of gene products at the single cell level.

By the use of specific nucleic acid (RNA or DNA) probes, genetic markers for infection and other disease states may be detected. Certain genetic diseases are characterized by the presence of genes which are not present in normal tissue. Other diseased conditions are characterized by the expression of RNAs or RNA translation products (i.e. peptides or proteins) which are not expressed in normal cells. Some disease states are characterized by the absence of certain genes or gene portions, or the absence or alteration of expression of gene products or proteins. Antibody probes specific for target antigenic biopolymers have also been used to identify the presence of viral proteins or gene products.

Current methods allow the detection of these markers but are relatively time consuming and of limited sensitivity. Hybridization techniques are based on the ability of single stranded DNA or RNA to pair (or hybridize) with a complementary nucleic acid strand. This hybridization reaction allows the development of specific probes that can identify the presence of specific genes (DNA), or polynucleotide sequences for the transcription and expression of those genes (mRNA).

Solution hybridization methods which require the destruction of the cell and the isolation of the nucleic acids from the cell prior to carrying out the hybridization reaction sacrifice the cellular integrity, spatial resolution and sensitivity of detection. In situ hybridization allows the detection of RNA or DNA sequences within individual cells. In situ hybridization yields greater sensitivity than solution hybridization by means of eliminating the dilution of a particular target gene, nucleic acid, or protein by the surrounding and extraneous RNA and DNA of other cells. In situ hybridization also allows for the simultaneous detection of multiple substances, i.e. genes, nucleic acids or proteins within individual cells, permitting the identification of a particular cell expressing a cellular gene or viral sequence. In addition, since in situ hybridization analysis is performed and quantitated for single cells, minimal sample and reagents are required.

Prior to the present invention, in situ hybridization procedures were only capable of detecting nucleic acids present at greater than ten copies per cell. Such procedures required multiple steps and at least 4 hrs. to over 14 days to perform.

SUMMARY OF THE INVENTION

It is an object of the present invention to provide a fast, sensitive in situ hybridization procedure capable of detecting polynucleotides when present at a concentration as low as 1-5 copies per cell.

It is a further object of the present invention to provide a fast and sensitive in situ hybridization procedure capable of detecting more than one target molecule in an individual cell.

It is a further object of the present invention to provide an in situ hybridization procedure that could be carried out within about 5 minutes to four hours.

It is a further object of the present invention to provide an in situ hybridization procedure that could be quantitative for as few as 1-5 molecules of target nucleic acid per cell.

It is a further object of the present invention to provide an in situ hybridization procedure that could simultaneously detect multiple biopolymers.

It is a further object of the present invention to provide an in situ hybridization procedure that could be carried out in one step.

It is a further object of the present invention to provide an in situ hybridization procedure that could be carried out on cells in suspension.

It is a further object of the present invention to provide an in situ hybridization procedure that could eliminate the need for immobilization of cells or tissues onto a solid support before analysis.

It is a further object of the present invention to provide an in situ hybridization procedure which could deliver a probe to living cells, maintain the viability of the cells and record the occurrence of hybridization by chemical or physical means or by an effect on one or more biological properties of the cell or its components.

It is a further object of the present invention to be able to simultaneously detect and discriminate between the DNA, RNA and protein for the same gene in the same cell using the process of in situ hybridization.

It is a further object of the present invention to provide an assay kit for one step in situ hybridization.

The present invention provides a method for the detection of biopolymers within individual cells or tissue sections either in solution or after being deposited on a solid support. Optimization of each component of the procedure as provided by the present invention allows a rapid, sensitive hybridization assay which may be accomplished in one step. Target biopolymer molecules may be quantitated at a level of as few as 1-5 molecules per cell. This hybridization assay may be used to detect levels of polynucleotides in cells such as bone marrow and peripheral blood, in tumors, in tissue sections or in tissue cultured cells. The hybridization procedure of the present invention can detect polynucleotides in single cells with the sensitivity as few as 1-5 molecules per cell in as little as 5 minutes to 4 hours. This procedure also allows simultaneous detection of more than one different polynucleotide sequence in an individual cell. The present invention also allows detection of proteins and polynucleotides in the same cell.

Briefly, cells, either as single cell suspensions or as tissue slices may be deposited on solid supports such as glass slides. Alternatively, cells are placed into a single cell suspension of about $10^5$–$10^6$ cells per ml. The cells are fixed by choosing a fixative which provides the best spatial resolution of the cells and the optimal hybridization efficiency.

The hybridization is then carried out in the same solution which effects fixation. This solution contains both a fixative and a chaotropic agent such as formamide. Also included in this solution is a hybrid stabilizing agent such as concentrated lithium chloride or ammonium acetate solution, a buffer, low molecular weight DNA and/or ribosomal RNA (sized to 50 bases) to diminish non-specific binding, and a pore forming agent to facilitate probe entry into the cells. Nuclease inhibitors such as vanadyl ribonucleoside complexes may also be included.

To the hybridization solution is added a probe, to hybridize with a target polynucleotide. The most preferable probe is a single-stranded anti-sense probe. For hybridization to cellular RNA, a probe of approximately 75 to 150 bases in length is used. For hybridization to cellular DNA, a probe of approximately 15–50 bases is used. An antibody probe may be utilized to bind to a target protein or antigen. The hybridization solution containing the probe is added in an amount sufficient to cover the cells when using immobilized cells. When utilizing cells in suspension, a 3× concentrate of hybridization cocktail is added to the cells. Alternatively, the cells may be resuspended in the hybrid solution. The cells are then incubated at the prescribed temperature for at least 5 minutes. The probe is utilized at a high concentration of at least about 1 µg/ml of hybrid mix in order to give optimal results in this time frame.

The probes may be detectably labeled prior to the hybridization reaction. Alternatively, a detectable label may be selected which binds to the hybridization product. Probes may be labeled with any detectable group for use in practicing the invention. Such detectable group can be any material having a detectable physical or chemical property. Such detectable labels have been well-developed in the field of immunoassays and in general most any label useful in such methods can be applied to the present invention. Particularly useful are enzymatically active groups, such as enzymes (see *Clin. Chem.*, 22:1243 (1976)), enzyme substrates (see British Pat. Spec. 1,548,741), coenzymes (see U.S. Pat. Nos. 4,230,797 and 4,238,565) and enzyme inhibitors (see U.S. Pat. No. 4,134,792); fluorescers (see *Clin. Chem.*, 25:353 (1979); chromophores; luminescers such as chemiluminescers and bioluminescers (see *Clin. Chem.*, 25:512 (1979)); specifically bindable ligands; proximal interacting pairs; and radioisotopes such as $^3H$, $^{35}S$, $^{32}P$, $^{125}I$ and $^{14}C$.

The invention of the present application provides a means of carrying out the fixation, prehybridization, hybridization and detection steps normally associated with in situ hybridization procedures all in one step. By modifying the components of this "one-step" solution, a convenient temperature may be used to carry out the hybridization reaction. Furthermore, this application provides a hybridization assay which can be accomplished with viable or non-viable cells in solution. In either case, the assay is rapid, requiring as little as 1 to 5 minutes to complete, and sensitive, detecting as few as 1–5 molecules of polynucleotide within a cell.

The superior results of the invention of the present application are postulated to occur by preventing precipitation of cellular constituents onto mRNA or the covalent modification of mRNA, the destabilization of ribosomal RNA subunit binding, and promotion of accessibility of full length mRNA for hybrid formation by inducing single-strandedness in cellular RNA and/or DNA. The present invention arose out of the applicant's discovery of the strong correlation between cellular RNA single-strandedness and the rapid kinetics of hybridization which yielded a highly sensitive assay procedure.

In one aspect, the present invention provides a simple method to determine the optimal fixation/prehybridization/hybridization/detection conditions for any tissue type so that: (1) single molecules may be detected, (2) cellular morphology will be preserved and (3) the total reaction time will be reduced to 5 minutes to 4 hours.

Briefly, in order to predict the optimal conditions to achieve this rapid and sensitive hybridization, a cellular specimen in multiple samples, either in suspension or deposited on glass slides, are exposed first to a fixative and subsequently to a hybridization solution.

The fixative is selected from the group consisting of 95% ethanol/5% acetic acid, 75% ethanol/20% acetic acid, 50% methanol/50% acetone and 10% formaldehyde/90% methanol (all v/v). Other useful fixatives will be obvious to one skilled in the art as long as the fixative selected allows at least a 70% shift of double stranded to single stranded cellular polynucleotides while maintaining cellular spatial relationships. The duration of exposure to the fixative is from 1 to 180 min. Preferably, 1 to 30 min., and most preferably 20 min. The temperature of the fixation procedure is preferably $-20°$ C. to $50°$ C. and most preferably $20°$ C. A subsequent exposure to 70% ethanol/30% water for 0.5 min. to 20 min. at $-20°$ C. to $30°$ C. may be utilized if samples are to be stored prior to hybridization.

The hybridization solution consists of a chaotropic denaturing agent, a buffer, a pore forming agent, a hybrid stabilizing agent, non-specific nucleotides, and a target specific probe.

The chaotropic denaturing agent (Robinson, D. W. and Grant, M. E. (1966) *J. Biol. Chem.* 241: 4030; Hamaguchi, K. and Geiduscheck, E. P. (1962) *J. Am. Chem. Soc.* 84: 1329) is selected from the group consisting of formamide, urea, thiocyanate, guanidine, trichloroacetate tetramethylamine, perchlorate, and sodium iodide. Any buffer which maintains pH at least between 7.0 and 8.0 may be utilized.

The pore forming agent is for instance, a detergent such as polyoxyethylene 23 lauryl ether (Brij 35); polyoxyethylene 20 cetyl ether (Brij 58); sodium docecyl sulfate; 3-[(3-cholamidopropyl)-dimethylammonio]-1-propanesulfonate (CHAPS TM); polyoxyethylene ether CAS# 9002-93-1 (Triton X-100). Depending on the location of the target biopolymer, the pore-forming agent is chosen to facilitate probe entry through plasma, or nuclear membranes or cellular compartmental structures. For instance, 0.05% Brij 35 or 0.1% Triton X-100 will permit probe entry through the plasma membrane but not the nuclear membrane. Alternatively, sodium desoxycholate will allow probes to traverse the nuclear membrane. Thus, in order to restrict hybridization to the cytoplasmic biopolymer targets, nuclear membrane pore-forming agents are avoided. Such selective subcellular localization contributes to the specificity and sensitivity of the assay by eliminating probe hybridization to complementary nuclear sequences when the target biopolymer is located in the cytoplasm. Agents other than detergents such as fixatives may serve this function. Furthermore, a biopolymer probe may also be selected such that its size is sufficiently small to traverse the plasma membrane of a cell but is too large to pass through the nuclear membrane.

Hybrid stabilizing agents such as salts of mono- and di-valent cations are included in the hybridization solution to promote formation of hydrogen bonds between complementary sequences of the probe and its target biopolymer. Preferably lithium chloride or ammonium acetate at a concentration from 0.15M to 1.5M is used; most preferably, the concentration of lithium chloride is 0.8M.

In order to prevent non-specific binding of nucleic acid probes, nucleic acids unrelated to the target biopolymers are added to the hybridization solution at a concentration of 100 fold the concentration of the probe.

Specimens are removed after each of the above steps and analyzed by observation of cellular morphology as compared to fresh, untreated cells using a phase contrast microscope. The condition determined to maintain the cellular morphology and the spatial resolution of the various subcellular structures as close as possible to the fresh untreated cells is chosen as optimal for each step.

In addition, cellular nucleic acids were stained with about 50 $\mu$g/ml propidium iodide dye. This dye has a specific characteristic fluorescent emission (about 480 nm, green) when the nucleic acid is single-stranded and emits at a different wave length (about 615 nm, red) when the nucleic acid is double-stranded. The dye utilized may be dependent upon whether the target sequence for the particular assay is RNA or DNA. If the assay is to detect low copy numbers of DNA, then a DNA detecting dye such as acridine orange, tetrahydrofuran, methyl green, pyronin Y and azure B is used, and the nuclear DNA is analyzed for the amount of single or double-strandedness. If instead, the assay is to be used to detect low copy numbers of RNA, then RNA dyes such as Acridines, Azines, Xanthenes, Oxazines, and Thiazines are used and the cytoplasmic RNA is analyzed for the amount of single or double-strandedness. Regardless of whether the assay is used to analyze RNA or DNA, the optimal conditions are reached when the nucleic acid to be detected has undergone a 70% shift from double-strandedness to single-strandedness. When the shift of the secondary structure of the nucleic acid from double-strandedness to single-strandedness has reached at least 70%, and there is no decrease in the total amount of fluorescence, then the conditions have been adjusted according to the present invention and will permit optimal hybridization and detection of as few as 1-5 molecules of target nucleic acid within a single cell. Furthermore, the time required for optimal hybridization can be determined from the amount of time necessary for at least 70% of the cellular nucleic acid to become single-stranded.

In the most preferred embodiment, the hybridization assay of the present invention provides a method for assaying biopolymers in a cell sample having substantially intact membranes comprising a single step of incubating the cells with a fixation/hybridization solution containing a single-stranded RNA probe, and subsequently detecting the amount of probe hybridized to the target nucleic acid. The samples are then washed and the amount of target nucleic acids are determined by quantitation either photographically through a microscope with fluorescent capabilities or by direct reading of the fluorescence with an image analysis system such as a Meridian ACAS 470 work station (Meridian Instruments, Okemos, Mich.).

BRIEF DESCRIPTION OF THE DRAWINGS

FIG. 4 demonstrates the detection of oncogenes in normal peripheral blood by One-Step In Situ Hybridization.

FIG. 7 demonstrates the automated digital analysis of the fluorescence within cells after One-Step In Situ Hybridization. In panels A through C, K562 cells were analyzed for the presence of c-abl, c-sis, and c-myc genes. Panel D represents the control and the colors the digital imaging instrument assigns to emitted signals of different intensities. When these colors are represented over a cell the amount and subcellular location of the target cellular biopolymer and the hybridized probe can be seen.

DETAILED DESCRIPTION OF THE INVENTION

Treatment of Sample

1. Cells/Tissues on Solid Support

Figure 1B:
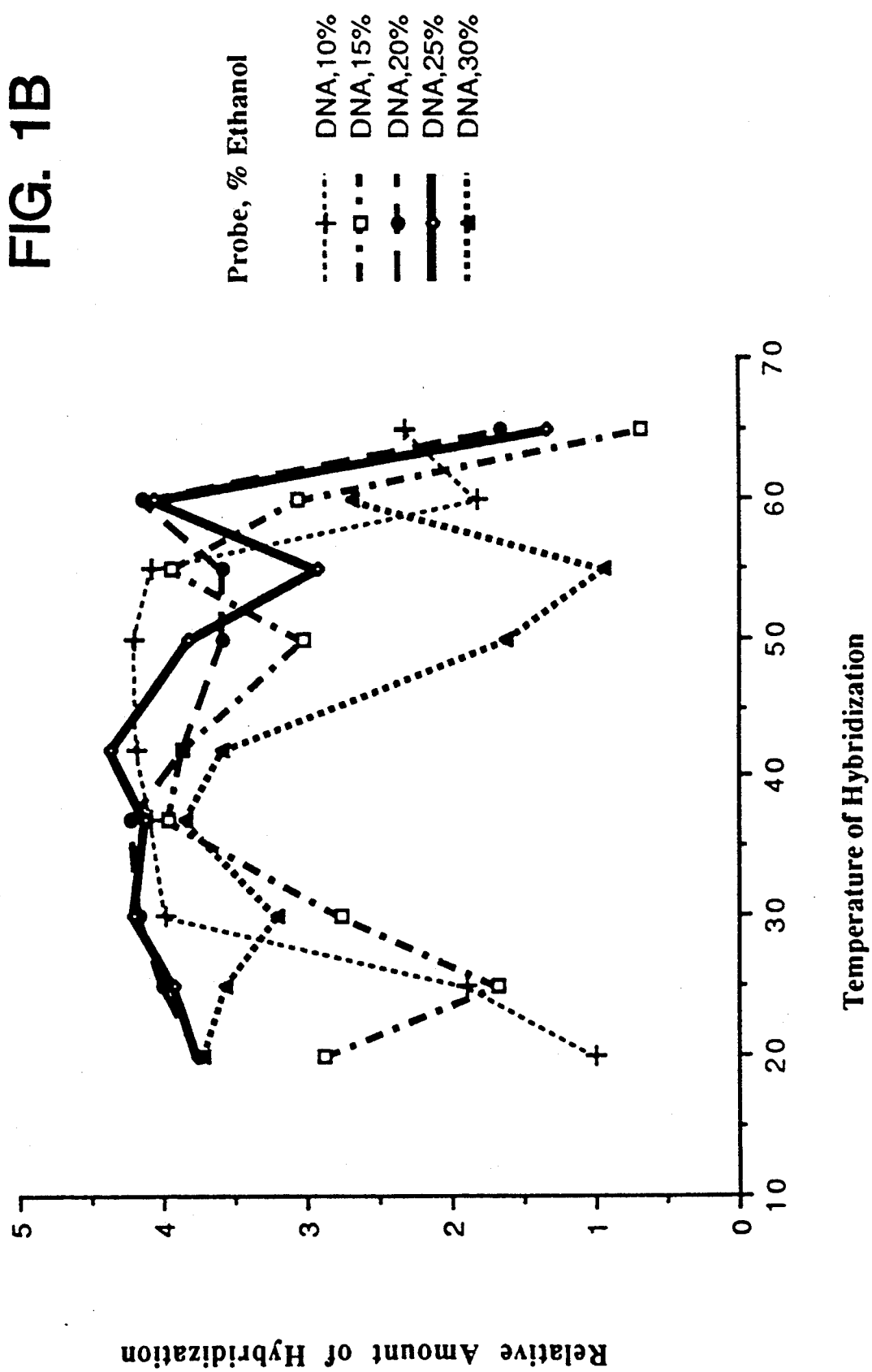
FIG. 1 demonstrates the optimal temperatures of one-step In Situ Hybridization.
FIG. 1A demonstrates that hybridization temperatures of 25° C. to 55° C. yield the most relative fluorescence corresponding to the most hybrid formation in the present in situ hybridization invention when RNA-DNA hybrids were formed within the cells. The results shown in FIG. 1B demonstrate that hybridization temperatures of 25°-55° may be used in the hybridization reaction when DNA—DNA hybrids are formed within the cells.

In one embodiment of this version of the One-Step in situ hybridization procedure of the present invention the specimen may be deposited onto a solid support. Specimens constitute any material which is composed of or contains cells or portions of cells. The cells may be living or dead, so long as the target biopolymer (DNA, RNA or protein) is unaltered and undamaged and capable of detection. The specimen should contain cells with substantially intact membranes. Although it is not necessary that all membranes of the cellular structure be intact, the membranes must be sufficiently preserved to allow: retention of the target biopolymer, introduction of the detecting probe to the site of the target biopolymer and preservation of antigenicity of any target membrane components.

Techniques for depositing the specimens on the solid support will depend upon the cell or tissue type and may include, for example, standard sectioning of tissue or smearing or cytocentrifugation of single cell suspensions.

Many types of solid supports may be utilized to practice the invention. Supports which may be utilized include, but are not limited to, glass, Scotch tape (3M), nylon, Gene Screen Plus (New England Nuclear) and nitrocellulose. Most preferably glass microscope slides are used. The use of these supports and the procedures for depositing specimens thereon will be obvious to those of skill in the art. The choice of support material will depend upon the procedure for visualization of cells and the quantitation procedure used. Some filter materials are not uniformly thick and, thus, shrinking and swelling during in situ hybridization procedures is not uniform. In addition, some supports which autofluoresce will interfere with the determination of low level fluorescence. Glass microscope slides are most preferable as a solid support since they have high signal-to-noise ratios and can be treated to better retain tissue.

The present invention may also be utilized to detect biopolymers in cells in suspension.

Regardless of whether the cell specimen is in suspension or on solid supports, the hybridization procedure is carried out utilizing a single hybridization solution which also fixes the cells. This fixation is accomplished in the same solution and along with the hybridization reaction. The fixative may be selected from the group consisting of any precipitating agent or cross-linking agent used alone or in combination, and may be aqueous or non-aqueous. The fixative may be selected from the group consisting of formaldehyde solutions, alcohols, salt solutions, mercuric chloride, sodium chloride, sodium sulfate, potassium dichromate, potassium phosphate, ammonium bromide, calcium chloride, sodium acetate, lithium chloride, cesium acetate, calcium or magnesium acetate, potassium nitrate, potassium dichromate, sodium chromate, potassium iodide, sodium iodate, sodium thiosulfate, picric acid, acetic acid, paraformaldehyde, sodium hydroxide, acetones, chloroform, glycerin, thymol, etc. Preferably, the fixative will comprise an agent which fixes the cellular constituents through a precipitating action and has the following characteristics: the effect is reversible, the cellular morphology is maintained, the antigenicity of desired cellular constituents is maintained, the nucleic acids are retained in the appropriate location in the cell, the nucleic acids are not modified in such a way that they become unable to form double or triple stranded hybrids, and cellular constituents are not affected in such a way so as to inhibit the process of nucleic acid hybridization to all resident target sequences. Choice of fixatives and fixation procedures can affect cellular constituents and cellular morphology; such effects can be tissue specific. Preferably, fixatives for use in the invention are selected from the group consisting of ethanol, ethanol-acetic acid, methanol, and methanol-acetone which fixatives afford the highest hybridization efficiency with good preservation of cellular morphology.

Fixatives most preferable for practicing the present invention include 10–40% ethanol, methanol, acetone or combinations thereof. These fixatives provide good preservation of cellular morphology and preservation and accessibility of antigens, and high hybridization efficiency.

Simultaneously, the "fixative" component of the solution may contain a compound which fixes the cellular components by cross-linking these materials together, for example, glutaraldehyde dimethylsuberimidate, ethyldimethylamino-propylcarbodiimide or formaldehyde. While this cross-linking agent must meet all of the requirements above for the precipitating agent, it is generally more "sticky" and causes the cells and membrane components to be secured or sealed, thus, maintaining the characteristics described above. The cross linking agents when used are preferably less than 10% (v/v).

Cross-linking agents, while preserving ultrastructure, often reduce hybridization efficiency; they form networks trapping nucleic acids and antigens and rendering them inaccessible to probes and antibodies. Some also covalently modify nucleic acids preventing later hybrid formation.

Typically, 20%-30% ethanol, 5% formalin and 5% acetone are used as a fixative for most tissues including peripheral blood, bone marrow, breast, lung, cervical sections, cardiac and skeletal muscle, and eye.

Prehybridization Treatments

According to the present invention no prehybridization step is necessary. Blocking nonspecific binding of probe and facilitating probe entry can be accomplished in the fixation/hybridization solution.

Hybridizations

Nucleic acid hybridization is a process where two or more mirror images or opposite strands of DNA, RNA, oligonucleotides, polynucleotides, or any combination thereof recognize one another and bind together through the formation of some form of either spontaneous or induced chemical bond, usually a hydrogen bond. The degree of binding can be controlled based on the types of nucleic acids coming together, and the extent of "correct" binding as defined by normal nucleic acids coming together, and the extent of "correct" binding as defined by normal chemical rules of bonding and pairing. For example, if the binding of two strands forms 9 out of 10 correct matches along a chain of length 10, the binding is said to be 90% homologous.

Cellular nucleic acid sequences are detected by the process of molecular hybridization. The probe must be "labeled" in some way so to allow "detection" of any complementary cellular nucleic acid sequences present within the individual cells.

In the present invention, the term "hybridization" also means the binding of an antibody to a target antigen.

Types of Probes

A probe is defined as genetic material DNA, RNA, or oligonucleotides or polynucleotides comprised of DNA or RNA and antibodies. The DNA or RNA may be composed of the bases adenosine, uridine, thymidine, guanine, cytosine, or any natural or artificial chemical derivatives thereof. The probe is capable of binding to a complementary or mirror image target cellular genetic sequence through one or more types of chemical bonds, usually through hydrogen bond formation. The extent of binding is referred to as the amount of mismatch allowed in the binding or hybridization process; the extent of binding of the probe to the target cellular sequences also relates to the degree of complementarity to the target sequences. The size of the probe is adjusted to be of such size that it forms stable hybrids at the desired level of mismatch; typically, to detect a single base mismatch requires a probe of approximately 12-50 bases. Larger probes (from 50 bases up to tens of thousands of bases) are more often used when the level of mismatch is measured in terms of overall percentage of similarity of the probe to the target cellular genetic sequence. The size of the probe may also be varied to allow or prevent the probe from entering or binding to various regions of the genetic material or of the cell. Similarly, the type of the probe (for example, using RNA versus DNA) may accomplish these objectives. The size of the probe also affects the rate of probe diffusion, probability of finding a cellular target match, etc. Typically, double-stranded DNA (dsDNA), single-stranded DNA (ssDNA) or RNA probes are used in a hybridization reaction when oligonucleotide sequences are the target.

Nucleic acid probes can be prepared by a variety of methods known to those of skill in the art. Purified double-stranded sequences of DNA (dsDNA) can be labeled intact by the process of nick translation or random primer extension. The ability of double-stranded probes to hybridize to nucleic acids immobilized within cells is compromised by the ability of the complementary strands to hybridize to each other in solution prior to hybridization with the cellular nucleic acids. Single-stranded DNA (ssDNA) probes do not suffer this limitation and may be produced by the synthesis of oligonucleotides, by the use of the single-stranded phage M13 or plasmid derivatives of this phage, or by reverse transcription of a purified RNA template. The use of single-stranded RNA (ssRNA) probes in hybridization reactions potentially provides greater signal-to-noise ratios than the use of either double or single-stranded DNA probes. Regardless of whether a dsDNA, a ssDNA, or a ssRNA probe is used in the hybridization reaction, there must be some means of detecting hybrid formation. The means of detecting hybrid formation utilizes a probe "labeled" with some type of detectable label.

Antibody probes are known to those of skill in the art. The term "antibody probe" means an antibody that is specific for and binds to any target antigen. Such a target antigen may be peptide, protein, carbohydrate or any other biopolymer to which an antibody will bind with specificity.

Detection Systems

Detectable labels may be any molecule which may be detected. Commonly used detectable labels are radioactive labels including, but not limited to, $^{32}P$, $^{14}C$, $^{125}I$, $^3H$ and $^{35}S$. Biotin labeled nucleotides can be incorporated into DNA or RNA by nick translation enzymatic, or chemical means. The biotinylated probes are detected after hybridization using avidin/streptavidin, fluorescent, enzymatic or colloidal gold conjugates. Nucleic acids may also be labeled with other fluorescent compounds, with immunodetectable fluorescent derivatives or with biotin analogues. Nucleic acids may also be labeled by means of attaching a protein. Nucleic acids cross-linked to radioactive or fluorescent histone Hl, enzymes (alkaline phosphatase and peroxidases), or single-stranded binding (ssB) protein may also be used. To increase the sensitivity of detecting the colloidal gold or peroxidase products, a number of enhancement or amplification procedures using silver solutions may be used.

An indirect fluorescent immunocytochemical procedure may also be utilized (Rudkin and Stollar (1977) Nature 265: 472; Van Prooijen, et al (1982) Exp.Cell.Res. 141: 397). Polyclonal antibodies are raised against RNA-DNA hybrids by injecting animals with poly(rA)-poly(dT). DNA probes were hybridized to cells in situ and hybrids were detected by incubation with the antibody to RNA-DNA hybrids.

According to the present invention single-stranded probes are preferable. Probes may be directly labeled by attachment of an intercalating detectable molecule with fluorescers or by covalently-binding to the probe such fluorescers. The probe may be labeled with more than one molecule of the detectable label.

Probe Size and Concentration

The length of a probe affects its diffusion rate, the rate of hybrid formation, and the stability of hybrids. According to the present invention, to detect cellular target RNA, small probes (50-150 bases) yield the most sensitive, rapid and stable system. A mixture of short probes (50–150 bases) are prepared which span the entire length of the target biopolymer to be detected. For example, if the target biopolymer were 1000 bases long, about 10–20 "different" probes of 50–100 bases would be used in the hybrid solution to completely cover all regions of the target biopolymer.

To detect cellular target DNA, even smaller probes (15–50 bases) are utilized.

The concentration of the probe affects several parameters of the in situ hybridization reaction. High concentrations are used to increase diffusion, to reduce the time of the hybridization reaction, and to saturate the available cellular sequences. According to the present invention, the reaction is complete after about 5 minutes. To achieve rapid reaction rates while maintaining high signal-to-noise ratios, probe concentrations of 1–10 μg/ml are preferable. Most preferable is use of probes at a concentration of 2.5 μg/ml.

Hybridization Solution and Temperature

The fixation/hybridization solution of the present invention consists of a fixative (described above) and a chaotropic agent, typically, 0.8M LiCl, about 0.1M Tris-acetate, pH 7.4, about 50 μg/ml low molecular weight DNA, and 50 μg/ml ribosomal RNA sized to about 50 bases and 0.1% Triton X-100. A single-stranded RNA probe is added to this solution prior to the incubations with the target cells. The probe may be at least 15–20 bases, preferably, 75–150 bases, and labeled with a detectable label such as a fluorescer. The most preferable optimal temperature of hybridization is 50°–55° C. However, temperatures ranging from 15° C. to 80° C. may be used, depending on the constituents and concentrations of the fixation/ hybridization solution.

Post-Hybridization Treatments and Detections

The present invention does not require wash steps prior to hybrid detections. If probes are labeled with Photobiotin ™, then avidin or streptavidin fluorescent, enzymatic or collodial gold complexes may be added directly to the slides containing hybridization cocktail and incubated for 20 minutes at room temperature, or 10 minutes at 37° C. or 5 minutes at 55° C. This step constitutes a significant advantage over prior hybridization techniques due to the time saved by eliminating several post-hybridization washing steps and the necessary re-blocking of non-specific avidin/streptavidin binding sites; it results in no decrease in signal or increase in noise. If probes are directly labeled with fluorescers, no additional detection step is necessary.

Following a streptavidin/avidin detection step or directly after the reaction is complete, the specimen is washed in large volumes of 2× SSC/0.1% Triton X-100. The solution may contain RNase A and T1 at room temperature. This wash can be very short (about 5 minutes)-as long as a continuous gentle circulation or stream of sufficient volume (about 200 ml per cm$^2$ area of cells) of solution passes over the cells. This may be followed by washes at higher stringency (lower salt concentrations such as at least 0.1× SSC and/or higher temperatures up to 65° C.). Leaving the cell area moist, supports are then dried and coverslipped by any conventional method.

2. Cells or Tissues in Suspension

Cells are Prepared

Tissue samples are broken apart by physical, chemical or enzymatic means into single cell suspension. Cells are placed into a PBS solution (maintained to cellular osmolality with bovine serum albumin (BSA)) at a concentration of $10^5$ to $10^6$ cells per ml. Cells in suspension may be fixed and processed at a later time, fixed and processed immediately, or not fixed and processed in the in situ hybridization system of the present invention.

Fixation/Hybridization is accomplished

A single solution is added to the cells/tissues (hereafter referred to as the specimen). This solution contains the following: a mild fixative, a chaotrope, a nucleic acid probe (RNA or DNA probe which is prelabeled) and/or antibody probe, salts, detergents, buffers, and blocking agents. The incubation in this solution is carried out at 55° C. for 20 minutes.

The fixative is one which has been found to be optimal for the particular cell type being assayed (e.g., there is one optimal fixative for bone marrow and peripheral blood even though this "tissue" contains numerous distinct cell types). The fixation is usually a combination of precipitating fixatives (such as alcohols) and cross-linking fixatives (such as aldehydes), with the concentration of the cross-linking fixatives kept very low (less than 10%). Typically, the solution contains 10–40% ethanol, and 5% formalin. The concentration and type of precipitating agent and crosslinking agent may be varied depending upon the probe and the stringency requirements of the probe, as well as the desired temperature of hybridization. Typical useful precipitating and cross-linking agents are specified in Table 1.

TABLE 1

TISSUE SPECIFIC EFFECT OF FIXATIVES

| | 70% EtOH | 95% EtOH 5% HAc | 75% EtOH 20% HAc | 100% MeOH | 100% Acetone | 50% MeOH 50% Acetone | PLP | 4% PF | 0.1% Glut | 10% Formaldehyde 90% Methanol |
|---|---|---|---|---|---|---|---|---|---|---|
| Cardiac Muscle | ND | +1 | +2 | +1 | +1 | +3 | ND | +1 | +1 | |
| Fibroblasts | +1 | +3 | +2 | +2 | +2 | | ND | +1 | +1 | ND |
| HL-60 | +3 | | +2 | +1 | +1 | +3 | +1 | +1 | +1 | +3 |
| K-562 | +3 | +2 | | +1 | +1 | +3 | +1 | +1 | +1 | ND |
| Normal Bone Marrow | +2 | | +3 | +1 | +2 | | +1 | +1 | +1 | ND |
| Normal Peripheral Blood | +3 | +3 | | +1 | +1 | +2 | +1 | +1 | +1 | +3 |

The hybridization cocktail contains a denaturing agent, usually formamide at 30% (v/v), but other chaotropic agents such as NaI, urea, etc. may also be used. Furthermore, several precipitating and/or cross-linking fixatives also have mild denaturing properties; these properties can be used in conjunction with the primary denaturant in either an additive or synergistic fashion. The hybridization cocktail may be constructed to preferentially allow only the formation of RNA—RNA or RNA-DNA hybrids. This is accomplished by adjusting the concentration of the denaturing agents along with the concentration of salts (primarily monovalent cations of the Group I series of metals along with the ammonium ion) and along with the temperature of hybridization which is used. This allows for the selective hybridization of probe to either cellular RNA or DNA or both RNA and DNA simultaneously with distinct probes. This further allows the probes to be supplied in a premixed solution which presents the optimal conditions for generating a signal and minimizing noise while simultaneously optimally "fixes" the morphology of the cells/tissues.

Hybrids are detected.

The probe in the hybridization cocktail may be labeled before the hybridization reaction. The label may be one of the many types described above. If the probe is labeled with Photobiotin TM, the hybrids may be detected by use of a Streptavidin/Avidin (S/A) conjugated to a fluorescent molecule such as FITC, rhodamine, Texas Red TM, etc. or to S/A conjugated to an enzyme or to S/A labeled with a heavy metal such as colloidal gold. Specifically, a solution containing the streptavidin conjugate is added directly to the hybridization cocktail over the cells after the end of the hybridization reaction. The cells are incubated in this solution for 5 minutes at 55° C. Longer times of hybridization may be used along with both higher or lower temperatures. The time of hybridization reaction will vary depending on the composition of the hybridization cocktail containing the fixative (type and concentrations of precipating agents and/or cross-linking agents), buffering agents, pore forming agents, denaturing agents and hybrid stabilizing agents. Similarly, the temperature may be varied as described above.

Alternatively, the probes may be directly labeled with the fluorescent dye or molecules such as Pontamine Sky Blue TM by incubating the nucleic acid probe and dye together (1:10 weight:weight proportions) and allowing the dye to bind/intercalate. The probe is then precipitated out of solution and the excess unbound dye is removed by repeated washing with 70% ethanol. Probes are also labeled directly and covalently by incubation of double stranded molecules (RNA—RNA, RNA-DNA, or DNA—DNA) with labels which will covalently bind to nucleic acids. After incubation conditions under which the reaction will take place, the strands are separated and each separate strand is used as a probe. The concentration of the probe in the solution is typically 2.5 µg/ml although a range of 0.01-10 µg/ml is useful. The probe concentration will affect the reaction kinetics and may affect the sensitivity of the assay along with the signal-to-noise ratio.

If the probe is labeled directly with an enzymatic label or is detected using an enzymatic or secondary detectable system, then this reaction may be carried out before any wash steps. Following the incubation of the specimen with the appropriate buffer for the enzyme, the slide is incubated with the substrates for the enzyme under conditions specified by the manufacturer or supplier of the enzyme.

Noise is Washed Away.

Cells may be deposited onto slides or centrifuged into a pellet following the fixation/hybridization/ detection reaction(s). Next, the unbound probe is washed away from the cells by one wash step using a solution of $0.1 \times$ SSC ($1\times$ SSC=0.15M NaCl and 0.015 M sodium citrate, pH 7.4) with 0.1% Triton X-100 TM. A total of 1-200 ml of wash solution may be used per microscope slide (i.e., per about 100,000 separated cells or per tissue section of about 1 square centimeter). The concentration and type of the hybrid stabilizing/denaturing agents and pore forming agents may be varied depending on the type of cells, the type of probe and the acceptable level of mismatch of the hybrid.

Results are obtained.

When cells are deposited onto slides, results are visualized manually on a fluorescent microscope when direct or indirectly labeled fluorescent probes are utilized. Alternatively, the results may be automatically analyzed on a fluorescence-based image analysis system such as the ACAS 470 Workstation TM which is produced by Meridian Instruments. If other types of labels are utilized on the probes, the means of detection is varied accordingly.

When cells are maintained in solution, results may be obtained using a flow cytometer to record the amount of fluorescence per cell, which represents the amount of hybrid per cell. Alternatively, the total signal within a cellular sample may be determined using a device such as a liquid scintillation counter (for radioactivity) or a chemiluminescent/fluorescent microtiter plate reader for these labels.

Analysis of the Results of In Situ Hybridizations Speed, Sensitivity and Quantitation of In Situ Hybridizations The method of the present invention requires 5 minutes to 4 hours to complete with a sensitivity of as few as 1-5 molecules of target biopolymers per cell. This results from the combination of at least three factors: 1) cellular constituents are not irreversibly precipitated onto the nucleic acids, 2) the fixation was optimized for the particular tissue used, and 3) the kinetics of the reaction proceed more rapidly at high probe concentrations, simultaneously with the fixation process and at elevated temperatures.

The number of copies of mRNA per cell can be estimated from the number of grains over cells when radioactive probes are used. With fluorescent or enzymatic detections a relative estimate of fluorescence or precipitated colored products allows estimation of mRNA copy number. Usually, the approximation of copy number is easier after manual photography, film processing and comparisons of photographic prints.

The quantitation of radioactive or fluorescent signals obtained after in situ hybridizations may be automated by use of an image analysis system such as the Meridian ACAS 470 Workstation TM.

Simultaneous Detection of Multiple Biopolymers

The present invention allows simultaneous detection of different substances (such as mRNAs and proteins) within the same cells. This may be accomplished in one of two ways. First, multiple probes each containing a unique label (for example, fluorescent tags "A", "B" and "C" which each emit light at a different detectable wave length) are all added together in the hybridization solutions. Alternatively, a hybridization and detection reaction may be carried out with one probe and label, residual unreacted probe and label washed away under nuclease-free conditions, and another hybridization reaction is carried out. This process is repeated as many times as desired.

Simultaneous Detection of DNA and RNA for the Same Gene

The present invention allows the simultaneous detection of DNA and RNA (and protein) for the same gene discriminately and concurrently within the same cell. This was accomplished in one of two ways. First, multiple probes each containing a unique label (for example, fluorescent tags "A", "B" and "C" which emit light at different detectable wavelengths) were all added together in the fixation/hybridization solution. Alternatively, a fixation/hybridization/detection reaction was carried out with one probe and label, residual unreacted probe and label was washed away under nuclease free conditions and another fixation/hybridization reaction was carried out. This process was repeated as many times as desired.

When DNA and RNA were both detected, the selection of the type of probe became important. When the cellular target biopolymer is RNA, an anti-sense, single stranded DNA probe was used in the assay. If the cellular target DNA is the biopolymer to be detected, a sense-strand, single-stranded RNA probe would be used in the assay. This probe selection, and the selection and concentration of components of the fixation/hybridization solution would allow only RNA-DNA hybrids to be formed. Therefore, the probe could only bind to the desired target cellular biopolymer; other nucleic acids would inherently be prevented from interfering with the reaction assay.

The present invention may be provided in the form of a kit. The kit of the present invention is used to detect the presence of a specific target biopolymer in a specimen. Such a kit includes the following:

1. A solution containing a fixation/hybridization cocktail and one or more labeled probes. Preferably, this solution will contain 15–40% ethanol, 25–40% formamide, 0–10% formaldehyde, 0.1–1.5M LiCl, 0.05–0.15M Tris-acetate (pH 7–8), 0.05%–0.15% Triton X-100, 20 ug/ml–200 ug/ml of a non-specific nucleic acid which does not react with the probe(s), and 0.1 ug/ml to 10 µg/ml of a single stranded probe directly labeled with a reporter molecule. Most preferably, this solution will contain 30% ethanol, 30% formamide, 5% formaldehyde, 0.8M LiCl, 0.1M Tris-acetate (pH 7.4), 0.1% Triton X-100, 50 µg/ml of ribosomal RNA sheared and sized to about 50 bases, and 2.5 µg/ml of a single stranded probe directly labeled with a fluorescent reporter molecule. This solution and the probes would have measurable predefined and identified characteristics and reactivities with cells and target sequences.

2. Means and instructions for performing the said in situ hybridization reaction of the present invention.

Alternatively, the kit may also include:

1. A second detectable reporter system which would react with the probe or the probe-target hybrid.

2. Concentrated stock solution(s) to be diluted sufficiently to form wash solution(s).

3. Any mechanical components which may be necessary or useful to practice the present invention such as a solid support (e.g. a microscope slide), an apparatus to affix cells to said support, or a device to assist with any incubations or washings of the specimens.

4. A photographic film or emulsion with which to record results of assays carried out with the present invention.

Another version of this kit may include a solution of probes encapsulated in liposomes or microspheres, as described in Examples 10 and 11.

The following examples are offered by way of illustration and are not intended to limit the invention in any manner. In all examples, all percentages are by weight if for solids and by volume if for liquids, and all temperatures are in degrees Celsius unless otherwise noted.

EXAMPLE 1

Preparation of Probes.

A. General

RNA or DNA probes useful in the present invention may be prepared according to methods known to those of skill in the art or may be obtained from any commercial source. RNA probes may be prepared by the methods described by Green et al. (1981) *Cell* 32:681. DNA probes may be prepared by methods known to those of skill in the art such as described by Rigby et al. (1977) *J. Mol. Biol.* 113:237. Synthetic oligonucleotide probes may be prepared as described by Wallace et al (1974) *Nucleic Acids Res.* 6: 3543. The probes useful in the present invention must have the following characteristics:

1. Specific for the target molecule.
2. At least 15 base pairs in length and preferably 75–150 base pairs.

B. Preparation of RNA probes.

Sub genomic fragments of the c-myc, c-sis, or c-abl genes were obtained from Amersham Inc. (Catalogue nos. RPN.1315X, RPN.1324X, and RPN.1325X, respectively). In one embodiment of the present invention, sense strand probe of the c-myc, c-abl and c-sis genes were utilized. The c-myc probe used was a 1.3 kb ClaI/EcoRI genomic clone from the 3' end of the c-myc gene (Dalla-Favera, et al. (1983) *Science* 219:963). The c-abl probe was derived from a subclone of the human c-abl gene, an EcoRI/Bam HI fragment corresponding to the 5' c-abl hybridizing region (de Klein et al. (1982) *Nature* 300:765). The c-sis probe was a Bam HI fragment of clone L33 corresponding to the 3' end of c-sis (Josephs et al. (1983) *Science* 219:503). The HIV and EBV probes were obtained from and prepared as described in Dewhurst, et al. (1987) *FEBS Lett.* 213:133. The CMV probe was described in Groncz̈ol, et al. (1984) *Science* 224:159. These template plasmid DNAs were transcribed as described by Green et al. (1981) Cell 32: 681. The size and quantity of the RNA were confirmed by electrophoresis through a denaturing agrose gel as described by Thomas (1980) *Proc. Nat. Acad. Sci. USA* 77: 5201 and by spectrophotometric measurement performed at $A_{260}$ and $A_{280}$. A DNA beta-actin probe, prepared as described in Cleveland, et. al. (1980) *Cell* 20:95, and the RNA probes were labeled with Photobiotin ™ as described by Bresser and Evinger-Hodges (1987) *Gene Anal. Tech.* 4: 89, incorporated herein by reference. Alternatively, probes were labeled directly with a fluorescent intercalating compound such as ethidium bromide, mithramycin, Pontamine Sky Blue ™, or propidium iodide by incubating the nucleic acid and dye together overnight at room temperature in 1:10 (w/w) proportions (nucleic acid/dye).

In either labeling method, low-molecular weight DNA was added at a concentration of 100 times that of the probe, and all polynucleotides were precipitated by the addition of ⅓ vol. 10M ammonium acetate and 2½ vol. of 95% ethanol. The nucleic acids were recovered by centrifugation and resuspended in water at a concentration of 1 ug/ul of probe and stored at −70° C. until used.

C. Preparation of Antibody Probes

Antibody probes specific for antigens such as viruses or specific determinants thereof, peptides and proteins derived from a variety of sources, carbohydrate moieties and a wide variety of biopolymers are known to those of skill in the art. The methods for preparation of such antibodies are also known to those of skill in the art.

Briefly, polyclonal antibodies may be prepared by immunization of an animal host with an antigen. Preferably, the antigen is administered to the host subcutaneously at weekly intervals followed by a booster dose one month after the final weekly dose. Subsequently, the serum is harvested, antibodies precipitated from the serum and detectably labeled by techniques known to those of skill in the art.

Monoclonal antibodies may be prepared according to any of the methods known to those in the art. Fusion between myeloma cells and spleen cells from immunized donors has been shown to be a successful method of producing continuous cell lines of genetically stable hybridoma cells capable of producing large amounts of monoclonal antibodies against target antigens such as, for instance, tumors and viruses. Monoclonal antibodies may be prepared, for instance, by the method described in U.S. Pat. No. 4,172,124 to Koprowski, et al. or according to U.S. Pat. No. 4,196,265 to Koprowski, et al.

Procedures for labeling antibodies are known to those of skill in the art.

EXAMPLE 2

Temperature effect on Hybridization.

K562 cells (ATCC # CCL 243) were grown in Hank's Balanced Salt Solution (HBSS) supplemented with 10% fetal calf serum. Dividing cells were deposited onto glass slides by cytocentifugation. Cells were fixed/hybridized with various concentrations of ethanol (10%, 15%, 20%, 25%, and 30%), 5% glacial acetic acid, 35% formamide, 5% formalin, 0.8M LiCl, 0.1% Triton X-100, 100 μg/ml low molecular weight DNA (sheared herring sperm DNA obtained from Sigma Chemical Company) and 2.5 μg/ml of either c-myc, c-abl or c-sis anti-sense RNA or DNA probes labeled with Photobiotin TM. The anti-sense RNA probes were prepared as described in Example 1. The hybridization reactions were carried out at various temperatures ranging from 4° to 80° C. After incubation at the desired temperatures for two hours, hybrid formation was detected. To detect hybridization, streptavidin fluorescein or rhodamine complexes at 2× the manufacter's recommended concentration was added to this specimen. After incubation at room temperature for 30 min the specimens were then gently washed (1 to 200 ml per centimeter square of cell area) with 0.1× SSC containing 0.1% Triton X-100. One drop of a 50/50 (v/v) 100% glycerol/2× PBS solution was added to each specimen. Using a Nikon fluorescent microscope with photomultipler tube attachments the fluorescence emitted per cell was recorded on each slide hybridized at a different temperature. Approximately 300 to 800 cells were analyzed per slide. Numerical results obtained indicating the amount of fluorescence from each cell were graphically represented as relative fluorescence verses the temperature of hybridization.

The results shown in FIG. 1A demonstrate that hybridization temperatures of 25° C. to 55° C. yield the most relative fluorescence corresponding to the most hybrid formation in the present in situ hybridization invention, with the above specified reagents and concentrations thereof when RNA-DNA hybrids were formed within the cells.

The results shown in FIG. 1B demonstrate that hybridization temperatures of 25°-55° may be used in the hybridization reaction when DNA-DNA hybrids are formed within the cells.

EXAMPLE 3

Kinetics of In Situ Hybridization.

K562 cells (ATCC # CCL 243) were grown in Hank's Balanced Salt Solution (BSS) supplemented with 10% fetal calf serum. Dividing cells were deposited onto glass slides by cytocentifugation. Cells were fixed/hybridized with 30% ethanol, 35% formamide, 5% formalin, 0.8M LiCl, 0.1% Triton X-100, 100 μg/ml low molecular weight DNA (sheared herring sperm DNA obtained from Sigma Chemical Company) and 2.5 μg/ml of either c-myc, c-abl or c-sis anti-sense RNA probe labeled with Photobiotin TM. The anti-sense RNA probes were prepared as described in Example 1.

Figure 2:
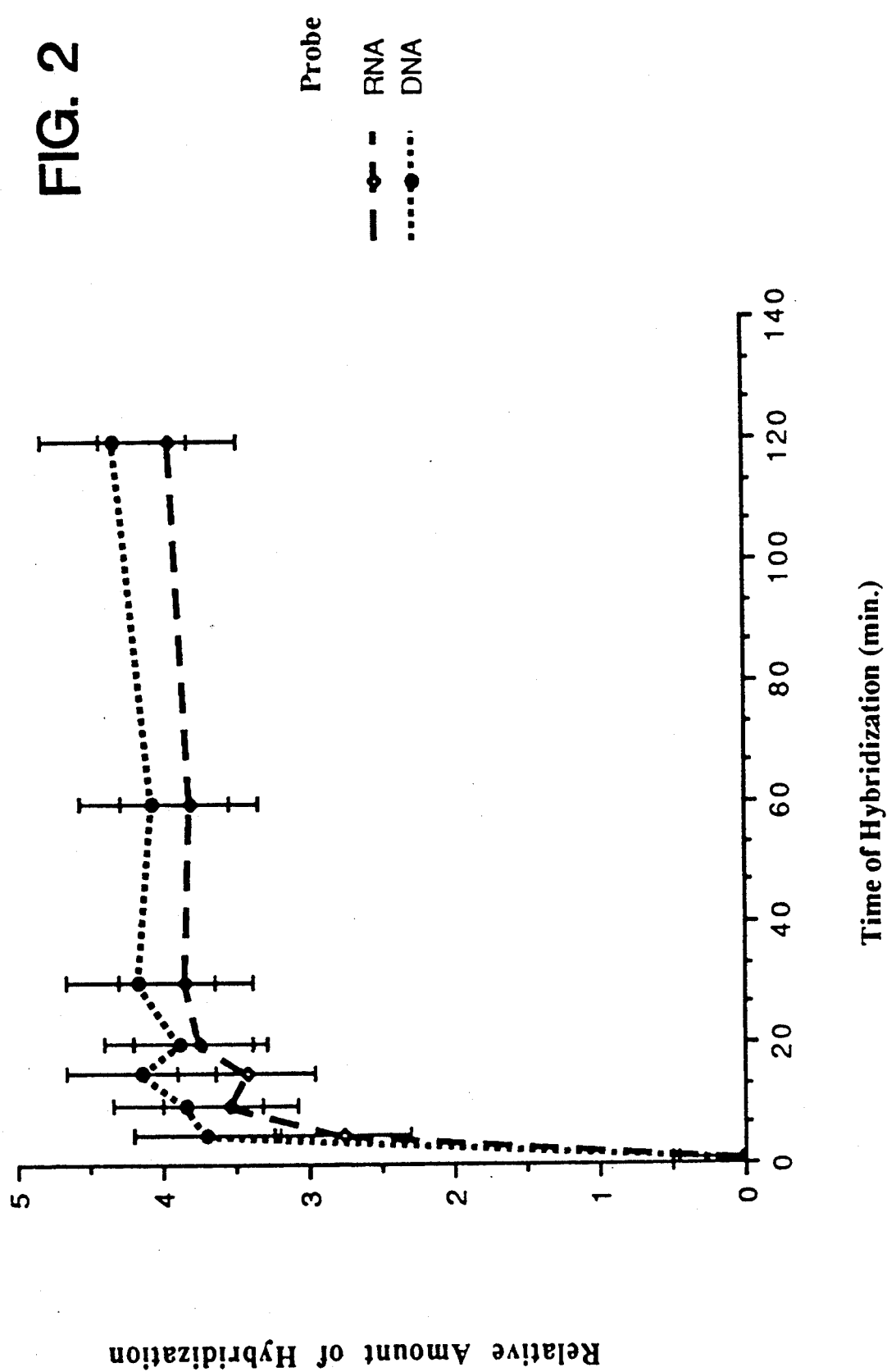
FIG. 2 demonstrates the kinetics of the One-Step In Situ Hybridization reaction.

FIG. 2 shows the relationship between the time of hybridization and the amount of fluorescence signal seen over cells. The hybridization reactions were carried out at various times ranging from 5 minutes to 96 hours. After incubation at 55° C. for the desired time, hybrid formation was detected. To detect hybridization, streptavidin fluorescein or rhodamine complexes at 2× the manufacturer's recommended concentration were added to the specimen. After incubation at room temperature for 30 minutes the specimens were then gently washed with 0.1× SSC/0.1% Triton X-100 at 1-200 ml per cm$^2$ of cell area. One drop of a 50/50 (v/v) 100% glycerol/2× PBS solution was added to each specimen. Using a Nikon fluorescent microscope with photomultiplier tube attachments, the fluorescence emitted per cell was recorded on each slide hybridized at each different time point. Approximately 300 to 800 cells were analyzed per slide. Numerical results obtained indicating the amount of fluorescence from each cell were graphically represented as relative fluorescence versus the time of hybridization. FIG. 2 demonstrates that the hybridization reaction is essentially complete after 5-10 minutes under the conditions of the present invention.

EXAMPLE 4

Chances in Secondary Structure Of Cellular RNA.

HL60 cells (ATCC # CCL 240) were grown in Hank's BSS supplemented with 10% fetal calf serum. Cells were harvested and deposited onto glass microscope slides by cytocentrifugation. Cells were air dried on glass slides and stored at room temperature until used. Cells are fixed in one of any number of fixatives for this type of experiment. Typical fixatives would include 70% ethanol, 95% ethanol/5% glacial acetic acid, 75% ethanol, 20% glacial acetic acid, 100% methanol, 100% acetone, 50% acetone, 50% methanol, 4% paraformaldehyde, 2% paraformaldehyde, 10% formaldehyde/90% methanol. After cells were fixed in these fixatives at the appropriate time and temperature, slides were removed from the fixative and stained with Wright Giemsa or hematoxylin and eosin by standard laboratory methods. Cell morphology was assessed by comparing the degree of preservation of morphology after fixation to the morphology prior to fixation. Fixatives which did not effectively retain visual morphology were arbitrarily rated as +1. Fixatives which effectively retained cellular morphology were arbitrarily rated as between +1 and +4 with the most effective morphologic preservation of cellular morphology rated as +4. A second evaluation as to the effective preservation of cells by these fixatives was carried out when it was desirable to detect cellular antigens. In this case, cells were removed from the fixatives and incubated with an antibody specific for a particular target cellular antigen. Again fixatives which effectively maintain antigenicity of cellular components were arbitrarily rated as +4, while fixatives which did not effectively maintain preservation of cellular antigens were rated lower, the worst as +1. Fixatives which scored as +3 or +4 in terms of preservation of cellular morphology and/or preservation of cellular antigenicity were then used in the following steps. Fresh slides containing untreated cells were fixed in these fixatives and were incubated in hybridization solution containing 50% formamide, 4× SSC, 0.1M sodium phosphate, (pH 7.4), 0.1% Triton X-100, 100 µg/ml low molecular DNA (sheared herring sperm DNA obtained from Sigma Chemical Company). No biopolymer probe was included in this solution. The cells were incubated in hybridization solution at 50°–55° C. for 5, 10, 15, 20, 30, 45, 60, 90, and 120 minutes. After the completion of this hybridization step, cell samples were washed gently with 1–200 ml per square centimeter of cell area with each of the following solutions containing 0.1% Triton X-100: 2× SSC, 1× SSC, 0.5× SSC, 0.1× SSC. The cellular sample was then evaluated as above for preservation of cellular morphology and/or preservation of cellular antigenicity. The cell sample was then further evaluated by staining the cells with 50 µg/ml of propidium iodide. The propidium iodide will stain double stranded and single stranded nucleic acids within the cell. When this dye stains double stranded or single stranded nucleic acids it has a different characteristic emission spectra upon ultraviolet excitation. An untreated cell sample on a slide is also stained. The total amount of emitted fluorescence is determined on the untreated cell sample using a Nikon fluorescence microscope with a photomultiplier tube attachment. 300–1000 cells are recorded as to the total amount of fluorescence generated from cytoplasmic double stranded RNA content. This measurement then represents a base line level for the total fluorescence in the cytoplasm; that is, the total RNA in the cytoplasm and that RNA being present in a 100% state of double strandedness. The slides which have been taken through the various fixation and hybridization procedures and times are similarly analyzed. In all cases it is important to chose a fixation and hybridization condition and time which will maintain the same quantity of fluorescence in the cytoplasm of the cell. During hybridization, the fluorescence emitted from the RNA of the cytoplasm of the cell due to the staining of the propidium iodide will change. The emission pattern decreases relative to the double strandedness of the RNA. Simultaneously, the wave length emission which is reflective of the amount of single stranded RNA in the cytoplasm will begin to increase. When the total fluorescence in the cytoplasm due to RNA has remained the same and the amount of fluorescence due to the amount of double stranded RNA in the cytoplasm has decreased approximately 70% while the amount of fluorescence corresponding to the single stranded RNA within the cytoplasm has increased an equal value, then conditions have been obtained which will allow the detection of 1–5 molecules of RNA within the cytoplasm. The time of the hybridization reaction which was required to obtained this shift from double stranded to single strandedness of the RNA in the cytoplasm is reflective of the time necessary for an actual hybridization reaction to detect 1–5 molecules per cell of RNA.

Figure 3:
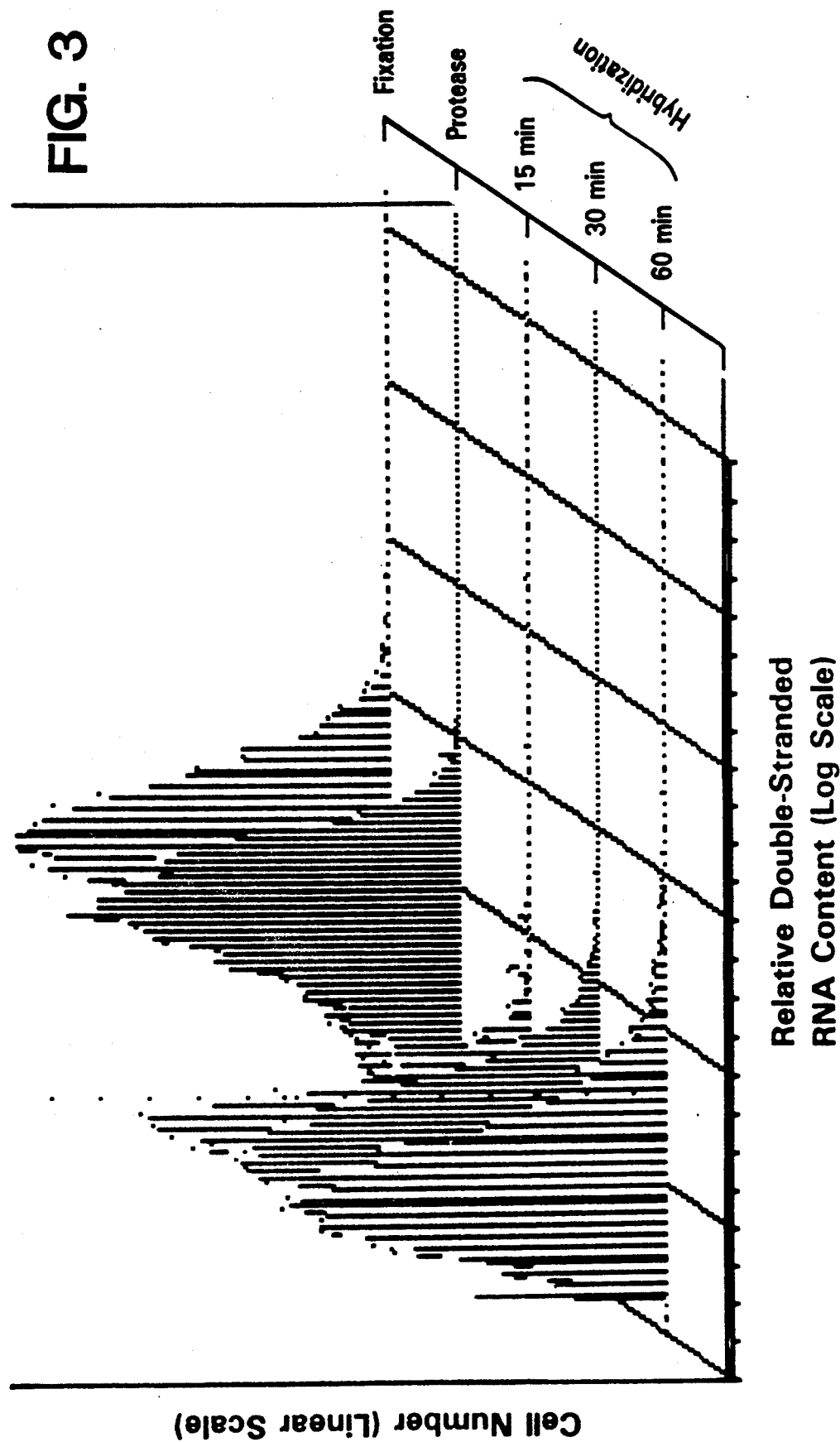
FIG. 3 demonstrates the changes in secondary structure of cellular RNA as a function of efficiency of the In Situ Hybridization reaction.

Specifically, in FIG. 3 the relative amount of double stranded RNA content is graphically represented on the bottom scale. As the RNA in the cytoplasm becomes more double stranded, the curves will shift to the right. The greater the shift in the amount of double strandedness to single strandedness of RNA in the cytoplasm, the greater the shift of the curves will be from the right to the left. The vertical axis represents the cell numbers that were counted. In other words if 300–1000 cells were counted, the vast majority of them fell within a particular area of double strandedness. While some cells had more double strandedness and some had less double strandedness, the analysis can be represented as a bell shape curve. On the right hand side of the figure is shown the various treatments carried out. The result of staining untreated cells with propidium iodide is not shown. However, after treating HL60 cells with various fixatives the amount of double strandedness of cellular RNA remained essentially the same. Even if a Prehybridization treatment is carried out which includes a protease treatment there is essentially no change in the amount of RNA double strandedness. The curve in FIG. 3 corresponding to the protease treatment is in the same location as the curve for the fixation treatment. It has shifted neither left nor right. However, after fifteen minutes in a hybridization solution, the curve representing the amount of RNA double strandedness has shifted at least 70% to the left. This corresponds to a change in at least 70% of the amount of material in the cytoplasm of the cell becoming single stranded. Comparing this graph to FIG. 2 indicates that after 15 min in the hybridization cocktail, not only is 70% of the RNA in the cytoplasm of the cell single stranded, but as seen in FIG. 2, 70% of the hybridization reaction is complete.

EXAMPLE 5

Detection of Oncogenes in Peripheral Blood Cells

Ten ml of human peripheral blood cells were incubated at 37° C. in a 1.2% (215 mOs) ammonium oxalate solution to lyse the red blood cells. The white blood cells were centrifuged at 3,000 rpm for 10 minutes in a clinical centrifuge. The cell Pellet was subsequently washed with 10 ml. PBS and the pellet was resuspended in PBS. Cells were deposited by cytocentrifugation onto precleaned glass slides and air dried for 5 min. The cells were then fixed and hybridized in a solution consisting of 30% ethanol/1% glacial acetic acid, 30% formamide, 0.8M LiCl, 0.1M Tris-acetate (pH 7.4), 0.1% Triton X-100, 100 µg/ml low molecular weight DNA (sheared herring sperm DNA obtained from Sigma Chemical Co.) and 2.5 µg/ml of either c-myc, c-sis, c-abl, anti-sense RNA probes labeled with Pontamine Sky Blue ™. The antisense RNA probes were prepared as described in Example 1. After incubation for 10 min. at 55° C., hybrid formation was detected.

The specimens were then gently washed (1–200 ml per cm² of cell area) with a solution containing 0.1% Triton X-100, 0.1× SSC. One drop of a 50/50 (v/v) 100% glycerol/2× PBS solution was added to each specimen. Specimens were photographed with high speed film (Kodak EES135, PS 800/1600) at 1600 ASA for 5 sec. exposure on a Nikon Photophot microscope at 400× magnification using a standard filter combination for transmission of fluorescent light.

Figures 4A, 4B, 4C:
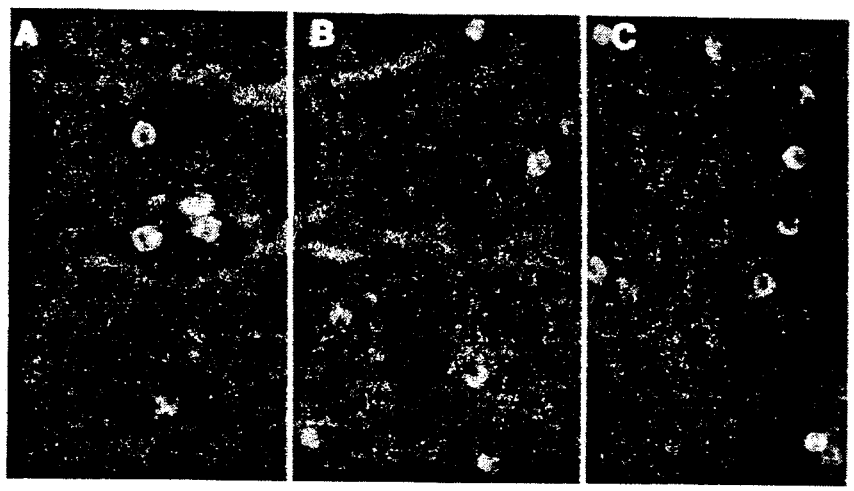
FIG. 4A shows the detection of the c-abl gene; 4B shows detection using a c-sis probe; and 4C shows that a typical result when cells are hybridized with the c-myc probe.

FIG. 4 depicts the results from in situ hybridization studies on the expression of three different oncogenes in peripheral blood (PB). FIG. 4A demonstrates the detection of the c-abl gene. Panel B shows the results of in situ hybridization with a c-sis probe. Panel C presents a typical result when the cells were hybridized with the c-myc probe.

EXAMPLE 6

Oncogene Detection in Solid Tissue.

Four micron thick frozen sections of human breast tissue obtained from surgically removed biopsy samples were mounted on precleaned glass slides.

Tissue was fixed and hybridized for 20 minutes by incubation at 55° C. with a fixation/hybridization (One Step) cocktail, containing 20% ethanol, 30% formamide, 0.8M LiCl, 0.1M Tris-acetate (pH 7.4, 50 µg/ml of low molecular weight denatured herring sperm DNA, 50 µg/ml of ribosomal RNA sheared and sized to 50 bases, and 0.1% Triton X-100. Pontamine Sky Blue TM labeled RNA probes (as described in Example 1) were added to the hybridization cocktail at a concentration of 2.5 µg/ml. No probe was added to the "blanks". Slides were washed at room temperature in 2× SSC containing 0 1% Triton X-100, 100 µg/ml RNase A (Sigma), and sequentially diluted SSC solutions until the final wash in 0.1× SSC (1–200 ml per CM² of cell area).

Detection of the labeled probes was performed by photography with a Nikon Photophot microscope with fluorescence capabilities using Kodak Ektachrome EES-135 (PS 800/1600) film, exposed and push processed at 1600 ASA. A 10 second exposure time was consistently used to allow direct comparison of one photograph to another.

Figure 5:
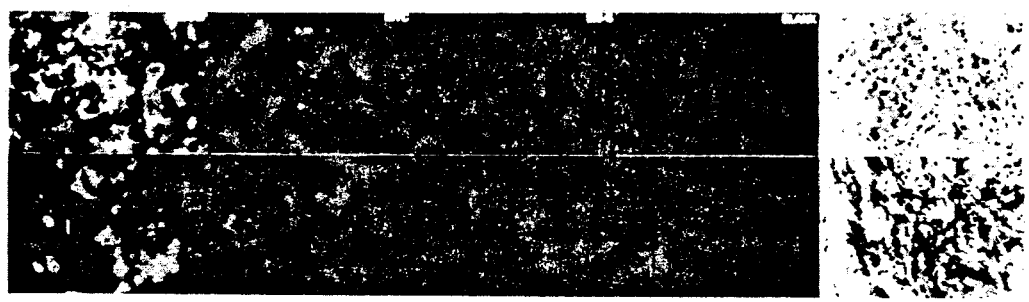
FIG. 5 demonstrates the detection of oncogenes in solid tissue samples by One-Step In Situ Hybridization. Panel SIS-AS demonstrates the results of the mRNA in situ hybridization assay and the localization of SIS/PDGF-B expression in the epithelial components of breast carcinoma. In panel MYC, an in situ hybridization reaction with the anti-sense c-myc RNA probe was used as positive control. In panel SIS-S, an in situ hybridization with the sense strand c-sis RNA probe was used as a negative control. Comparable histologic features are shown in the far right panel (Blank). Two cases of infiltrating ductal carcinoma are illustrated.

FIG. 5 demonstrates the results of the mRNA in situ hybridization assay and the localization of SIS/PDGF-B expression in the epithelial components of breast carcinoma (FIG. 5, panel SIS-AS). An in situ hybridization reaction with the anti-sense c-myc RNA probe was used as positive control (FIG. 5 Panel MYC); in situ hybridization with the sense strand c-sis RNA probe (FIG. 5 panel SIS-S) was used as a negative control. Comparable histologic features are shown in the far right panel. Two cases of infiltrating ductal carcinoma are illustrated.

EXAMPLE 7

Detection of HIV in Human Peripheral Blood.

Ten ml of human peripheral blood was incubated at 37° C. in a 1.2% ammonium oxalate solution to lyse the red blood cells. The white blood cells were centrifuged at 3,000 rpm for 10 minutes in a clinical centrifuge. The cell pellet was subsequently washed with 10 ml PBS and the Pellet was resuspended in PBS. Cells were deposited by cytocentrifugation onto precleaned glass slides and air dried for 5 min. The cells were then fixed and hybridized in a solution consisting of 25% ethanol, 30% formamide, 5% formalin, 0.8M LiCl, 0.1M Tris-acetate (pH 7.4), 0.1% Triton X-100, 100 µg/ml low molecular weight DNA (sheared herring sperm DNA obtained from Sigma Chemical Co.) and 2.5 µg/ml of either HIV anti-sense or sense strand RNA probes labeled with Pontamine Sky Blue TM. The RNA probes were prepared as described in Example 1. After incubation for 10 min. at 55° C., hybrid formation was detected.

The specimens were then gently washed (1–200 ml per cm² of cell area) with the following solution: 0.1% Triton X-100/ 0.1× SSC. One drop of a 50/50 (v/v) 100% glycerol/2× PBS solution was added to each specimen prior to coverslipping the specimen and microscopic examination. Specimens were photographed with high speed film (Kodak EES135, PS 800/1600) at 1600 ASA for 5 sec. exposure on a Nikon Photophot microscope at 400× magnification using a standard filter combination for transmission of fluorescent light.

Figure 6:
FIG. 6 demonstrates the detection of HIV in a seronegative, asymptomatic, high risk individual by One-Step In Situ Hybridization. Panel AS-HIV demonstrates hybridization with a cocktail containing antisense HIV RNA probes while panel S-HIV demonstrates that no hybridization is detectable using sense HIV RNA probes.

FIG. 6 demonstrates the detection of HIV sequences in human peripheral blood. FIG. 6, panel AS-HIV demonstrates hybridization with a cocktail containing anti-sense HIV RNA probes; FIG. 6 panel S-HIV demonstrates that no hybridization is detectable using sense HIV RNA probes. The present in situ hybridization invention detected HIV in a virus infected patient, while the negative controls were blank.

EXAMPLE 8

Quantitation of the Number of Target Biopolymer Molecules.

K562 Cells (ATCC #CCL 243) were grown in Hank's BSS supplemented with 10% fetal calf serum. Three days after the last change in media, the cells were split to a density of about $10^5$ cells per 0.3 ml. of fresh media One hour later, 60 replica slides were made by depositing 50,000–100,000 cells onto a slide by cytocentrifugation. The remainder of the cells were harvested and RNA and DNA was extracted from the cells by the guanidium cesium chloride method (GuSCN/CsCl) (Chirgwin, et al. (1979) *Biochemistry* 18: 5294).

Since the cell line was a relatively homogeneous population, the extracted RNA was purified and used to determine copy number estimates for each RNA species analyzed; i.e., an estimate could be made of the number of molecules of each gene present within each cell from a series of control experiments well known to those with knowledge and skill in the art. These control experiments to determine the number of molecules per cell included the following: Northern blots, RNA dot blots, Quick-blots TM, Cytodots TM, single copy saturation experiments, and solution concentration versus time hybridization experiments (Rot analysis) (Hames, B. D. and Higgins, S. J. (1986) in *Nucleic Acid Hybridization: a practical approach*, IRL Press, Oxford-Washington, D.C.).

Cells on slides were fixed and hybridized in a solution consisting of 25% ethanol, 30% formamide, 5% formalin, 0.8M LiCl, 0.1M Tris-acetate (pH 7.4), 0.1% Triton X-100, 100 µg/ml low molecular weight DNA (sheared herring sperm DNA obtained from Sigma Chemical Co.) and 2.5 µg/ml of an anti-sense RNA probe labeled with Pontamine Sky Blue TM. Probes used were either the sense or anti-sense RNA strands of the foliowing genes: c-abl, c-sis, c-myc, or Epstein Barr Virus (EBV).

The probes were prepared as described in Example 1. After incubation for 10 min. at 55° C., hybrid formation was detected.

The specimens were then gently washed (1-200 ml. per cm² of cell area) with 0.1× SSC containing 0.1% Triton X-100. One drop of a 50/50 (v/v) 100% glycerol/2× PBS solution was added to each specimen and a #1 coverslip was placed over the cells before microscopic examination.

Fluorescence emitted from each cell is a reflection of the number of fluorescent molecules which reacted with and attached to the probe; the amount of reacted probe within a cell is indicative of the number of target biopolymers present within the cell. To measure the fluorescence within each cell, slides were analyzed using the ACAS 470 Workstation ™ from Meridian Instruments (Okemos, Mich.) The Meridian instrument, like most image processing systems, excites the fluorescers present within a sample and then captures the emitted light as either a digital or analog signal. This signal is digital on the Meridian instrument. The quantity of the signal can be represented by different colors. In FIG. 7, this is illustrated by the colors the instrument assigns to emitted signals of different intensities. When these colors are represented over a cell, as in FIG. 7, the amount and subcellular location of the target cellular biopolymer and the hybridized probe can be seen.

Figure 8:
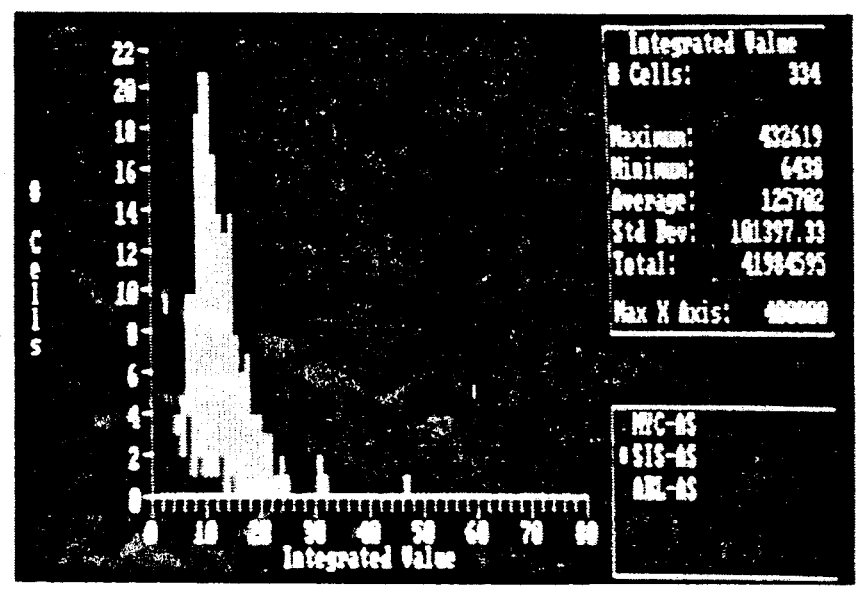
FIG. 8 demonstrates a quantitative analysis of One-Step In Situ Hybridization data.

The total amount of fluorescent signal per cell can also be detected and analyzed. From the control experiments carried out above to determine the number of molecules of mRNA corresponding to different genes within the K562 cells, known values (minimums, maximums, averages and standard deviations) are obtained for the number of molecules of each type of RNA per cell. These values are used as inputed data in the Meridian instrument's analysis of data, and are seen as the horizontal axis of FIG. 8. The vertical axis is the number of cells. The different columns represent the number of cells (vertical axis) possessing a given number of molecules (horizontal axis) of the target biopolymer. FIG. 8 demonstrates that the c-myc gene mRNA was present at the lowest level in the K562 cells (about 1-10 molecules). The c-sis gene MRNA was present at about 1-20 molecules. The c-abl gene mRNA was present in a much higher number of molecules per cell ranging from about 20-55 molecules.

EXAMPLE 9

In Situ Hybridization of mRNA Within Cells in Suspension

K562 cells (ATCC # CCL 243) were grown in Hank's Balanced Salts Solution (HBSS) supplemented with 10% fetal calf serum. Three days after the last medium change, the cells were split to a density of about $10^5$ cells per 0.3 ml of fresh medium. One hour later, cells were pelleted at 3000 rpm in a clinical centrifuge and resuspended at a concentration of $10^5$ to $10^6$ cells per ml in HBSS without serum. The cells were then processed by one of the following methods:

1. Cells were fixed.

Cells were fixed in solution consisting of 45% ethanol/5% formalin. This was done by adding an equal volume of a solution of 90% ethanol/10% formalin to the cell sample. Cells may be stored in this solution at 4° C. for at least several days. To carry out the in situ hybridization reaction, an equal volume of a solution consisting of 60% formamide, 4M ammonium acetate, 0.2M Tris-acetate (pH 7.4), 100 μg/ml of ribosomal RNA sheared and sized to 50 bases, and 5 μg/ml of an RNA probe directly labeled with fluorescein, prepared and labeled as described in Example 1, was added to the cell suspension. After incubation at 55° C. for 30 minutes, the cells were Pelleted by centrifugation at 3000 rpm in a clinical centrifuge. The cell pellet was washed three times with HBSS. In the final wash, the cells were resuspended at about 75,000 cells per 0.3 ml. The detection of hybrid formation was accomplished after the cells were deposited onto glass slides by cytocentrifugation. One drop of a 50/50 (v/v) 100% glycerol/2× PBS solution was added to each specimen and a #1 coverslip was placed over the cells before microscopic examination. Alternatively, flow cytometer instrumentation could also be used for the detection of hybrid formation.

Fluorescence emitted from each cell is a reflection of the number of fluorescent molecules which reacted with or were attached to the probe; the amount of reacted probe within the cells was therefore visualized and recorded through photomicroscopy using a Nikon Photophot fluorescence microscope. Specimens were photographed with high speed film (Kodak EES135, PS 800/1600) at 1600 ASA for 10 seconds exposure time and a 400× magnification using standard filter combinations for transmission of fluorescent light.

Figure 9:
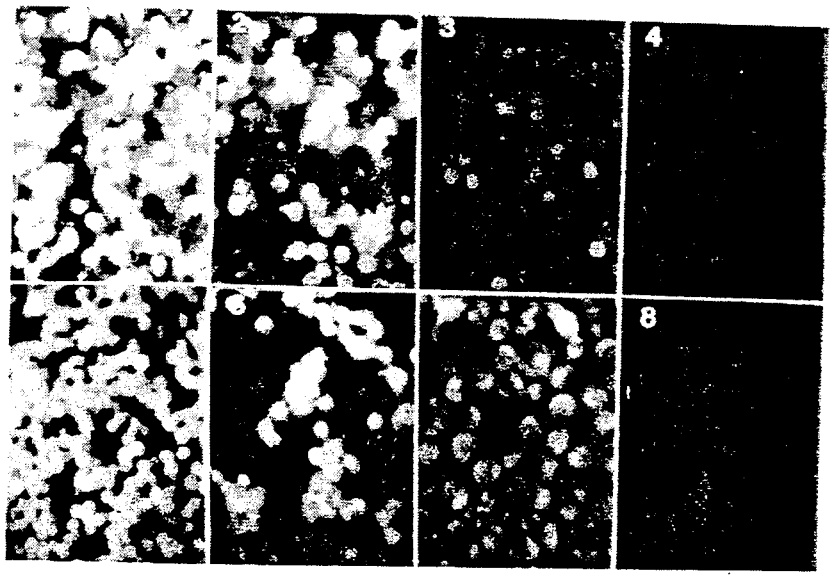
FIG. 9 demonstrates the One-Step In Situ Hybridization reaction performed on cells in solution. It is known that K562 cells express mRNA target nucleic acid sequences corresponding to the c-abl, c-sis, and c-myc oncogenes. The detection of the c-abl gene is shown in panel 1, as the light emitted from the cells; the detection of the c-sis gene is shown in panel 2, and the detection of the c-myc gene in panel 3 for cells which were fixed before the in situ hybridization reaction. Panel 4 shows that the background is negative when cells are fixed but no probe is included in the in situ hybridization reaction. The detection of the c-abl gene is shown in panel 5, as the light emitted from the cells; the detection of the c-sis gene is shown in panel 6, and the detection of the c-myc gene in panel 7 for cells not fixed before the in situ hybridization reaction. Panel 8 shows that the background is negative when cells are not fixed and no probe is included in the in situ hybridization assay.

The results are demonstrated in FIG. 9, panels 1-4. It is known that K562 cells express mRNA target nucleic acid sequences corresponding to the c-abl, c-sis, and c-myc oncogenes. The detection of the c-abl gene is shown in panel 1, as the light emitted from the cells; the detection of the c-sis gene is shown in panel 2, and the detection of the c-myc gene in panel 3. Panel 4 shows that the background is negative when no probe is included in the in situ hybridization reaction.

2. Cells were not fixed before the in situ hybridization assay.

To carry out the in situ hybridization reaction, an equal volume of the following solution was added to the cell suspension: a solution consisting of 35% ethanol, 55% formamide, 5% formalin, 4M ammonium acetate, 0.2M Tris-acetate (pH 7.4), 100 μg/ml of ribosomal RNA sheared and sized to 50 bases, and 5 μg/ml of an anti-sense RNA probe directly labeled with fluorescein, prepared and labeled as described in Example 1. After incubation at 37° C. for 20 minutes, the cells were pelleted by centrifugation at 3000 rpm in a clinical centrifuge. The cell pellet was washed three times with HBSS. In the final wash, the cells were resuspended at about 75,000 cells per 0.3 ml. The detection of hybrid formation was accomplished after the cells were deposited onto glass slides by cytocentrifugation. One drop of a 50/50 (v/v) 100% glycerol/2× PBS solution was added to each specimen and a #1 coverslip was placed over the cells before microscopic examination. Alternatively, instrumentation could also be used for the detection of hybrid formation such as a flow cytometer.

Fluorescence emitted from each cell is a reflection of the number of fluorescent molecules which reacted with probe; the amount of reacted probe within the cells was therefore visualized and recorded through photomicroscopy using a Nikon Photophot fluorescence microscope. Specimens were photographed with high speed film (Kodak EES135, PS 800/1600) at 1600 ASA for 10 seconds exposure time and at 400× magnification using standard filter combinations for transmission of fluorescent light.

The results are demonstrated in FIG. 9, panels 5–8. It is known that K562 cells express mRNA target nucleic acid sequences corresponding to the c-abl, c-sis, and c-myc oncogenes. The detection of the c-abl gene is shown in panel 5, as the light emitted from the cells; the detection of the c-sis gene is shown in panel 6, and the detection of the c-myc gene in panel 7. Panel 8 shows that the background is negative when no probe is included in the in situ hybridization assay.

EXAMPLE 10

In Situ Hybridization of mRNA within Cells in Suspension: Hybridization to HIV Sequences Within Viable Cells The T-cell derived cell line H9 (ATCC # CRL 8543) containing the pBH10 strain of HIV, the cell line K562 and the cell line HL60 were separately grown in medium consisting of Hank's Balanced Salt Solution supplemented with 10% fetal calf serum. Three days after the last change in media, the cells were split to a density of about $10^5$ cells per 0.3 ml of fresh media. One hour later, cells were pelleted at 3000 rpm in a clinical centrifuge and resuspended at a concentration of $10^5$ to $10^6$ cells per ml in HBSS without serum.

HIV anti-sense or sense RNA probes were prepared as described in Example 1 and labeled with Photobiotin ™. The probes were then encapsulated into reverse evaporation phase liposome vesicles (REVs) according to the method of Szoka (1978) *Biochemistry* 75: 4194. The liposomes were sterile filtered and stored at 4° C. for up to four weeks before use.

To carry out the in situ hybridization reaction, the REVs were added to the cell sample and a 30 minute or 60 minute incubation was carried out at 55° C. or 37° C., respectively. The cells were then pelleted by centrifugation at 3000 rpm for 10 minutes. The cell pellet was washed once with HBSS, pelleted again, and resuspended in HBSS supplemented with 10% serum; the cells were then allowed to continue to grow at 37° C. in an atmosphere of 5% $CO_2$ in air.

If the probes which were added to the cells had recognized and bound to a specific target cellular gene corresponding to the HIV virus, the function of that cellular target gene should be altered. To assay for the successfulness of the probe binding to a target viral sequence within a living cell, specific biological properties associated with the presence of active virus within a cell were assayed. The results of these biological assays are summarized on Table 2. H9 cells containing the pBH10 isolate of HIV were used as positive controls (HIV+). Uninfected H9 cells, HL60 cells and K562 cells were all used as negative controls (HIV−). No differences were seen between the 3 negative control cell lines with respect to any property tested. Syncytia formation was scaled after microscopic examination on a relative basis: −, no detectable syncytia; +, some detectable syncytia; +++, many syncytia seen. Changes in viral reverse transcriptase activity were measured relative to cells receiving no probe. HIV viral antigens were detected by indirect immunofluorescence. Antibodies directed to these antigens were supplied by Cellular Products, Inc. RNA and DNA were prepared by the GuSCN/CsCl method. Dot blots were prepared and hybridized to $^{32}$P-labeled double stranded DNA (ds-DNA) full length genomic probes. Hybridizations and wash conditions were stringent enough only to exclude detection of rRNA and other human endogenous retroviral sequences. Filters were exposed to film for a sufficient period of time to detect single copy sequences. Scoring was based on an arbitrary scale with infected H9 cells as an upper level control (+++).

The REVs containing the anti-sense HIV probes are referred to on the table as "Drug". The REVs containing negative control sense strand HIV probes are referred to on the table as "Drug Analog". REVs which contained no probe are referred to on the table as "No Drug".

TABLE 2

| | LABORATORY TREATMENT of HIV INFECTED (+) OR UNINFECTED (−) CONTROL CELL LINES (1) | | | | | | | | |
|---|---|---|---|---|---|---|---|---|---|
| | syncytia formation (2) | | percentage decrease in viral enzymes (3) | | detection of viral proteins (4) | | presence of viral RNA (5) | | presence of viral DNA (5) | |
| | HIV+ | HIV− | HIV+ | HIV− | HIV+ | HIV− | HIV+ | HIV− | HIV+ | HIV− |
| no drug | + | − | 0 | − | +++ | − | +++ | − | +++ | − |
| drug analog | + | − | 28 | − | +++ | − | +++ | − | +++ | − |
| drug | − | − | 99 | − | ± | − | +++ | − | +++ | − |

Table 2 summarizes the results demonstrating that the in situ hybridization procedure can introduce and cause hybrid formation between a probe and a specific target mRNA sequence and that the introduced anti-sense probe will inhibit the activity of the target mRNA. These biological assays included the inhibition of synctia formation, the inhibition of viral enzymes and proteins as well as the detection of viral RNA and DNA. Syncytia formation is a process wherein virus infected cells will tend to clump together into very large apparently multinucleated masses. The absence of syncytia formation in the "Drug" treated cells indicated that the probe was delivered to and hybridized with the specific cellular target sequences, thereby blocking the formation of syncytia. The enzyme reverse transcriptase is a virus specific enzyme. The greater than 99% decrease in the activity of this enzyme in virus infected cells, along with the lack of production of other viral proteins also demonstrates the successful inhibition of the expression of the viral phenotype by the hybridization of the anti-sense RNA probe to the cellular mRNA of the infected cells.

EXAMPLE 11

In Situ Hybridization of mRNA within Cells in Suspension: Hybridization to HIV Sequences Within Cells from Virus Infected Patients.

Ten ml of human peripheral blood from patients with AIDS, AIDS-related complex (ARC) or asymptomatic sero-positive individuals was diluted with twenty ml of HBSS and layered over a Ficoll-Hypaque ™ solution. The sample was centrifuged to separate the mononuclear cells. These cells were removed and placed into sterile culture with growth medium consisting of HBSS supplemented with 10% human serum/5% fetal calf serum. The medium was replaced after three days in culture. The cell lines K562 and HL60 were each grown in culture in HBSS containing 10% fetal calf serum. Three days after the last change in media, the cells were split to a density of about $10^5$ cells per 0.3 ml of fresh medium. One hour later, cells were pelleted at 3000 rpm in a clinical centrifuge and resuspended at a concentration of $10^5$ to $10^6$ cells per ml in HBSS without serum.

HIV anti-sense or sense RNA probes were prepared as described in Example 1 and labeled with Photobiotin TM. The probes were then encapsulated into reverse evaporation phase liposome vesicles (REVs) according to the method of Szoka (1978) *Biochemistry* 75: 4194. The liposomes were sterile filtered and stored at 4° C. for up to four weeks before use.

To carry out the in situ hybridization reaction, the REVs were added to the cell sample and a 30 minute or a 60 minute incubation was carried out at either 55° C. or 37° C., respectively. The cells were then pelleted by centrifugation at 3000 rpm for 10 mintues. The cell pellet was resuspended in HBSS supplemented with 10% serum and the cells were allowed to continue to grow.

When the probes are added to cells and bind to a specific target cellular gene within the cells corresponding to the HIV virus, the function of that cellular target gene is altered. To assay for the successfulness of the probe binding to a target viral sequence within a living cell, specific biological properties associated with the presence of active virus within a cell were assayed. The results of these biological assays are summarized on Table 3. The REVs containing the anti-sense HIV probes are referred to on the table as "Drug". The REVs containing negative control sense strand HIV probes are referred to on the table as "Drug Analog". REVs which contained no probe are referred to on the table as "No Drug". Table 3 summarizes the biological observation which documented that the present invention was capable of introducing and causing hybrid formation between a probe and a specific target mRNA sequence. These biological assays included the observation of whether cells formed syncytia. Since HIV realted viruses tend to inhibit cell proliferation, the increase in cell proliferation with the "Drug" treatment further demonstrated the success of delivery of the RNA probes to and hybridization with the mRNA in viable cells. The enzyme reverse transcriptase is a virus specific enzyme. The greater than 93% decrease in the activity of this enzyme in virus infected cells, along with the lack of production of other viral proteins also demonstrates the successful inhibition of the viral phenotype expression.

Figure 10:
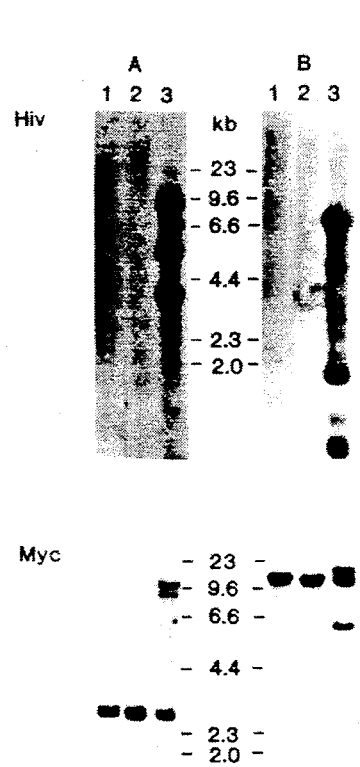
FIG. 10 demonstrates a Southern Blot.

FIG. 10 demonstrates that cells which do not contain the matching target sequences for the REV contained probe are not altered as to their DNA content by the present invention. FIG. 10 shows the results of a Southern blot of K562 cells treated with the REVs containing sense strand probes (Lanes A1 and B1) or REVs containing anti-sense strand probes (Lanes A2 and B2). The third lane on both the A and B columns is a positive control known to contain sequences which would react with either the sense or anti-sense strand probes. This demonstrates that the probe was degraded and does not cause a change in the cellular DNA when the REV delivered the probe to a cell which did not contain a matching target sequence.

Figure 11:
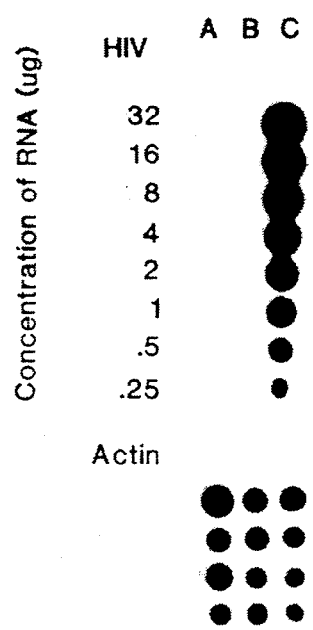
FIG. 11 demonstrates an RNA dot blot.

FIG. 11 demonstrates that cells which do not contain the matching target sequences for the REV contained probe were not altered as to their RNA content. In the top (HIV) panel, K562 cells which were treated with the sense probe (Lane A) or with the anti-sense probe (Lane B) did not contain any new cellular RNA corresponding to the probe or its complementary match. The third lane (C) demonstrates a positive control known to contain sequences which would react with either the sense or anti-sense strand probes, demonstrating that the probe is degraded and does not cause a change in the cellular RNA when the REV delivered the probe to a cell which did not contain a matching target sequence.

TABLE 3

NOVEL AIDS VIRUS THERAPEUTIC AGENT
Laboratory Treatment of Patient Blood (1,2)

| | syncytia formation (3) | cell proliferation (4) | percentage decrease in viral enzymes (5) | detection of viral proteins (6) | detection of viral antibodies (7) |
|---|---|---|---|---|---|
| no drug | + | − | 0 | + | + |
| drug analog | + | − | 14 | + | + |
| drug | − | + | 93 | − | − |

EXAMPLE 12

Detection of HIV and CMV in Human Peripheral Blood

Ten ml of human peripheral blood from a patient with Kaposis Sarcoma was incubated at 37° C. in a 1.2% ammonium oxalate solution to lyse the red blood cells. The white blood cells were centrifuged at 3,000 rpm for 10 minutes in a clinical centrifuge. The cell pellet was subsequently washed with 10 ml PBS and the pellet was resuspended in PBS. A number of replica slides were prepared by depositing 50,000–100,000 cells by cytocentrifugation onto precleaned glass slides. To these cells was added 20 ul of hybridization solution consisting of 30% ethanol, 30% formamide, 5% formaldehyde, 0.8M LiCl, 0.1M Tris-acetate (pH 7.4), 100 ug/ml low molecular weight DNA, 0.1% Triton X-100 and 2.5 ug/ml hybrid mix of either four HIV anti-sense or sense RNA probes or a CMV anti-sense RNA probe directly labeled with Pontamine Sky Blue TM. The RNA probes were prepared as described in Example 1. After incubation for 10 min. at 55° C., the specimens were gently washed (1–200 ml per cm2 of cell area) with 0.1× SSC containing 0.1% Triton X-100. One drop of a 50/50 (v/v) 100% glycerol/2× PBS solution was added to each specimen. Specimens were photographed with high speed film (Kodak EES135, PS 800/1600) for 5 sec. exposure on a Leitz microscope at 400× magnification using a standard filter combination for transmission of fluorescent light.

Figure 12:
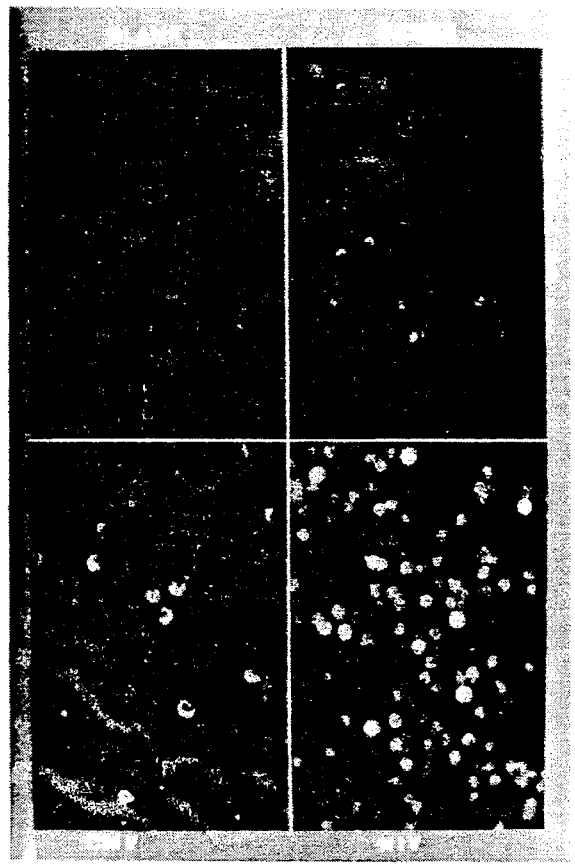
FIG. 12 demonstrates the detection by One-Step In Situ Hybridization of the Human Immune Deficiency Syndrome Virus (HIV) or Cytolmegalovirus (CMV) in the peripheral blood of a patient with Kapog's Sarcoma. The upper left panel ("BLANK") represents the results when no probe was added to the hybridization solution; the lower right panel ("HIV"), when four anti-sense strand HIV probes were added; the upper right panel ("SENSE"), when four sense strand HIV probes were added; and the lower left panel ("CMV"), when an anti-sense CMV probe was added.

FIG. 12, panel "BLANK" represents the results when no probe was added to the hybridization solution; panel "HIV", when four anti-sense strand HIV probes were added; panel "SENSE", when four sense strand HIV probes were added; and panel "CMV", when an anti-sense CMV probe was added. Two viruses (HIV and CMV) associated with HIV infection in Kaposi sarcoma were detected by the one-step in situ hybridization of the present invention.

EXAMPLE 13

Detection of Oncogenes in the K562 Cell Line

K562 cells (ATCC #CCL 243) were grown in HBSS supplemented with 10% fetal calf serum. One hour after the medium was changed, a number of replica slides were Prepared by depositing 50,000–100,000 cells onto a slide by cytocentrifugation. To these cells was added twenty ul of hybridization solution consisting of 20% ethanol, 30% formamide, 5% formaldehyde, 0.8M LiCl, 0.1M Tris-acetate (ph 7.4), 100 µg/ml low molecular weight DNA, 0.1% Triton X-100 and 2.5 µg/ml of either a c-myc, c-sis, or c-abl anti-sense RNA probe labeled directly with Pontamine Sky Blue ™. The probes were prepared as described in Example 1. After incubation for 10 minutes at 55° C., the specimens were gently washed (1–200 ml per cm$^2$ of cell area) with 0.1× SSC containing 0.1% Triton X-100. One drop of a 50/50 (v/v) 100% glycerol/2× PBS solution was added to each specimen and a #1 coverslip was placed over the cells before microscopic examination. Photographs were obtained as described in Example 12.

Figures 13A, 13B, 13C, 13D:
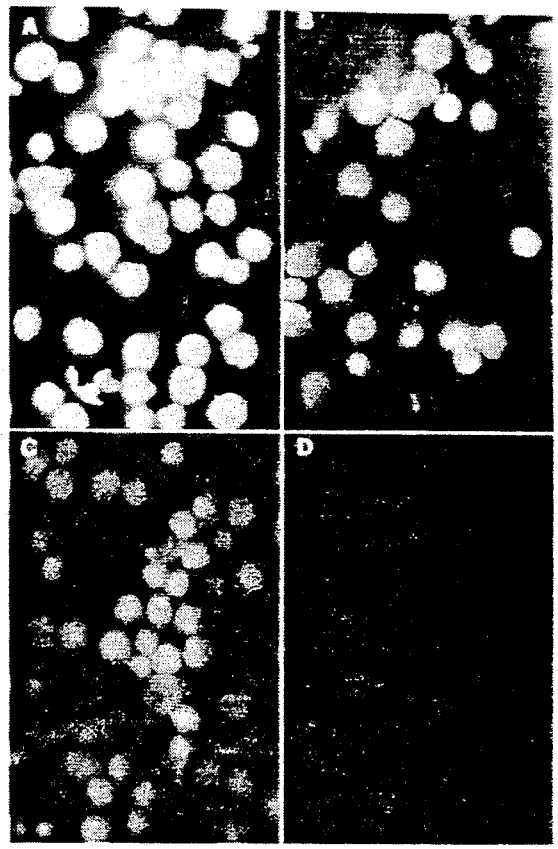
FIG. 13 demonstrates the detection by One-Step In Situ Hybridization of oncogenes in the cell line K562. Panel A demonstrates the results when c-abl anti-sense probe was added; panel B, when c-sis anti-sense probe was added; panel C, when c-myc anti-sense probe was added; and panel D, when no probe was added to the hybridization solution.

FIG. 13, panel D demonstrates the results when no probe was added to the hybridization solution; panel A, when c-abl anti-sense probe was added; panel C, when c-myc anti-sense probe was added; and panel B, when c-sis anti-sense probe was added. The one-step in situ hybridization procedure of the present invention detected 3 oncogenes known to be expressed in this cell line. The negative control (panel D) is blank.

One skilled in the art will readily appreciate that the present invention is well adapted to carry out the objects and obtain the ends and advantages mentioned, as well as those inherent therein. The components, methods, procedures and techniques described herein are presently representative of the preferred embodiments, are intended to be exemplary, and are not intended as limitations on the scope of the present invention. Changes therein and other uses will occur to those skilled in the art which are encompassed within the spirit of the invention and are defined by the scope of the appended claims.

What is claimed is:

1. A method for assaying biopolymers in a sample of cells having substantially intact membranes comprising the steps of:
   contacting said sample with a medium comprising a fixative agent, a denaturing agent, a hybrid stabilizing agent, a buffering agent, a membrane pore-forming agent and at least one probe, said contacting being under hybridizing conditions,
   incubating said sample with said medium in the presence of at least one detectable label, and
   detecting duplex formation by said probe(s) and target biopolymer(s) in said sample by means of said label, without performing a prehybridization step for blocking nonspecific binding of said probe(s) and facilitating probe entry before contacting said sample with said medium.

2. The method of claim 1 wherein said label is attached to said probe.

3. The method of claim 1 wherein said label is added after the duplex formation is complete.

4. The method of claim 1 wherein said label is selected from the group consisting of fluorescers, chemiluminescers, enzyme labels, and radiolabels.

5. The method of claim 3 wherein said label is selected from the group consisting of avidin and streptavidin.

6. The method of claim 1 wherein said fixative agent is selected from the group consisting of ethanol, methanol, acetone, formaldehyde and combinations thereof.

7. The method of claim 1 wherein said denaturing agent is selected from the group consisting of formamide, urea, sodium iodide, thiocyanate, guanidine, perchlorate, trichloroacetate, and tetramethylamine.

8. The method of claim 1 wherein said hybrid stabilizing agent is selected from the group consisting of sodium chloride, lithium chloride, magnesium chloride, ferric sulfate and ammonium acetate.

9. The method of claim 1 wherein said pore forming agent is selected from the group consisting of polyoxyethylene 23 lauryl ether, polyoxyethylene 20 cetyl ether, polyoxyethylene ether, 3-[3-cholamidopropyl)-dimethylammonio]-1-propanesulfonate, desoxycholateandsodiumdodecyl sulfate.

10. The method of claim 1 wherein said biopolymer is RNA.

11. The method of claim 1 wherein said biopolymer is DNA.

12. The method of claim 1 wherein said biopolymer is an antigen.

13. The method of claim 1 wherein at least two biopolymers are assayed simultaneously in the same sample.

14. The method of claim 13 wherein at least one biopolymer is a polynucleotide and a second biopolymer is an antigen.

15. The method of claim 1 wherein said temperature is 15° C.–80° C.

16. The method of claim 15 wherein said temperature is 50° C. to 55° C.

17. The method of claim 1 wherein said method is accomplished within about 4 hours.

18. The method of claim 1 wherein said biopolymer is selected from the group consisting of a RNA, a DNA, a viral gene, an oncogene, and an antigen.

19. The method of claim 1, wherein said biopolymer is an oncogene.

20. The method of claim 1, wherein said biopolymer is a virus.

21. A kit for assaying the presence of a suspect biopolymer in a cell sample comprising,
   a hybridization solution comprising a precipitating agent, a denaturing agent, a hybrid stabilizing agent, a buffering agent, and
   a membrane pore-forming agent.

22. The kit of claim 21 also comprising, a supply of a probe selected so that it will hybridize with said suspect biopolymer if it is present, to form a hybridized complex.

23. The kit of claim 22 also comprising,
   means for contacting said suspect sample with said probe to form said hybridized complex, and
   means for measuring for the presence and/or extent of the presence of such labeled probe.

24. The kit of claim 22 where in said probe is detectably labelled.

25. The kit of claim 22 also comprising,
   a detectable label capable of detecting hybrid formation.

26. A kit for assaying the presence of a biopolymer in a suspect cell sample comprising, a hybridization solution comprising 30% ethanol, 30% formamide, 5% formaldehyde, 0.8M LiCl, 0.1M Tris-acetate (pH 7.4), 0.1% polyoxyethylene ether, 50 µg/ml of ribosomal RNA sheared and sized to about 50 bases, and 2.5 µg/ml of a single stranded probe directly labeled with a fluorescent reporter molecule.

27. The kit of claim 26 also comprising, a supply of a probe selected so that it will hybridize with said suspect biopolymer if it is present, to form a hybridized complex.

28. The kit of claim 27 wherein said probe is detectably labeled.

29. The kit of claim 27 also comprising,
a detectable label capable of detecting hybrid formation.

30. The method of claim 1 wherein said detecting of hybrid formation is quantitative.

31. The method of claim 1 wherein said probe is a polynucleotide having a nucleotide sequence at least substantially complementary to a specific nucleotide sequence to be detected.

32. The method of claim 1 wherein said probe is an antibody directed toward a specific antigen.

33. The method of claim 1 wherein said detectable label is an energy emitting label.

34. The method of any of claims 1 or 21 wherein said probe comprises a mixture of short probes to multiple regions of the target biopolymer.

35. The method of claim 1 wherein the target biopolymer is a nucleic acid and said method is capable of detecting fewer than five copies of said nucleic acid per cell.

36. A method for assaying nucleic acids in a sample of cells having substantially intact membranes, consisting essentially of the steps of:
contacting said sample with a medium comprising a fixative agent, a denaturing agent, a hybrid stabilizing agent, a buffering agent, a membrane pore-forming agent and at least one nucleic acid probe, said contacting being under hybridizing conditions,
incubating said sample with said medium in the presence of at least one detectable label, and
detecting duplex formation by means of said label,
wherein said method is capable of detecting as few as five copies of a target nucleic acid per cell.

37. The method of claim 36, in which the sample is treated with a fixative before being contacted with said medium.

38. The method of claim 36, in which the contacting is carried out in solution.

39. The method of claim 36, in which the detecting is carried out by flow cytometry.

* * * * *